US010792497B2

(12) United States Patent
Matsuyama

(10) Patent No.: US 10,792,497 B2
(45) Date of Patent: Oct. 6, 2020

(54) FREQUENCY THERAPY DEVICE

(71) Applicant: Akemi Nishimura, Tokyo (JP)

(72) Inventor: Keisuke Matsuyama, Machida (JP)

(73) Assignee: Akemi Nishimura, Tokyo (JP)

( * ) Notice: Subject to any disclaimer, the term of this patent is extended or adjusted under 35 U.S.C. 154(b) by 0 days.

(21) Appl. No.: 16/489,724

(22) PCT Filed: Mar. 9, 2018

(86) PCT No.: PCT/JP2018/009339
§ 371 (c)(1),
(2) Date: Oct. 7, 2019

(87) PCT Pub. No.: WO2018/168719
PCT Pub. Date: Sep. 20, 2018

(65) Prior Publication Data
US 2020/0023180 A1    Jan. 23, 2020

(30) Foreign Application Priority Data

Mar. 14, 2017 (JP) .................................. 2017-049093
Aug. 31, 2017 (JP) .................................. 2017-167596

(51) Int. Cl.
*A61N 1/36* (2006.01)
*A61N 1/04* (2006.01)

(52) U.S. Cl.
CPC ......... *A61N 1/3603* (2017.08); *A61N 1/0492* (2013.01); *A61N 1/36021* (2013.01)

(58) Field of Classification Search
CPC .... A61N 1/0492; A61N 1/32; A61N 1/36021; A61N 1/3603
See application file for complete search history.

(56) References Cited

U.S. PATENT DOCUMENTS 5,658,322 A    8/1997  Fleming

FOREIGN PATENT DOCUMENTS

JP    S54-6311 Y2    3/1979
JP    H04-129571 A   4/1992
(Continued)

OTHER PUBLICATIONS

Jun. 12, 2018 English Translation of International Search Report issued in International Patent Application No. PCT/JP2018/009339.
(Continued)

*Primary Examiner* — Jonathan T Kuo
(74) *Attorney, Agent, or Firm* — Oliff PLC

(57) ABSTRACT

A frequency therapy device 10 is characterized by comprising a main device unit 20 that passes, between a pair of electrode pads 12, 12, a current corresponding to a predetermined voltage waveform, and a waveform memory 22 that is provided therein and stores a plurality of voltage waveforms at different frequencies, and in that: the waveform memory 22 stores the voltage waveforms in any of N waveform storage regions 22-1 to 22-N for each of N frequencies as waveform data comprising a square wave with a sampling frequency of 192 kHz or more and a number of quantization bits of 24 or more; the waveform data is read from the waveform memory 22 for each frequency, the waveform data is converted to an analog waveform by a D/A converter 24 during a preset time, and a current corresponding to the voltage waveform is passed between the electrode pads 12, 12; and the waveform memory 22 repeatedly and successively stores the waveform data for every set time for each frequency.

12 Claims, 16 Drawing Sheets

(56) References Cited

FOREIGN PATENT DOCUMENTS

| JP | 2003-305130 A | 10/2003 |
|---|---|---|
| JP | 2009-160328 A | 7/2009 |

OTHER PUBLICATIONS

Jun. 12, 2018 International Search Report issued in International Patent Application No. PCT/JP2018/009339.

FREQUENCY THERAPY DEVICE

TECHNICAL FIELD

The present invention relates to a frequency therapy device.

BACKGROUND ART

As shown in Patent Literature 1, a frequency therapy device including: a pair of electrode pads capable of being in contact with the human body with an affected part being interposed therebetween; and a control unit that passes, between the pair of electrode pads, a current corresponding to a voltage waveform in which a direction thereof is reversed at regularly repeated time intervals and a voltage increases and decreases alternately on a positive side and a negative side has been disclosed.

In this type of frequency therapy device, sequentially applying currents corresponding to a plurality of voltage waveforms at different frequencies to an affected part has also been known. In this case, for each of the voltage waveforms, the same waveform is repeatedly used to apply a current for a given length of time.

In such a conventional frequency therapy device, for each frequency, a voltage waveform is formed each time, or waveform data stored in a waveform memory is read, the data is converted to an analog waveform by a D/A converter, and a predetermined waveform is outputted.

In this case, the voltage waveform or the waveform data is a digital waveform generated by pulse width modulation (PWM). As compared to a case where an analog waveform is used as it is, spike-shaped part in a rise portion and a fall portion in the digital waveform depend on the number of quantization bits and the sampling frequency thereof. However, in a shorter wavelength, in particular, such spike-shaped part disappear.

Since spike part have been conventionally regarded as noise, no problem arises in that respect. In recent years, however, it has been increasingly recognized that a higher voltage in a frequency therapy device gives a greater impact on the human body and a greater impact results in a larger effect of pain relief, for example.

It can be readily envisaged that such a spike part can be formed with a square wave having a narrow width. According to a result (not publicly known), however, when there are only spike part without the presence of a subsequent high-level part or low-level part, one feels that the pain relief effect is small (this fact has not been known). This can be considered that voltages (absolute values) in the part (the high-level part and the low-level part) following the spike part, an impact given by a top peak part or bottom peak part of such a spike part deforms diseased cells, for example, and the high-level part and the low-level part keep the deformed state.

In the case of using a digital waveform, on the other hand, if a voltage is increased during use in a region of 2000 Hz or lower, especially in a low-frequency region of 1000 Hz or lower, exceeding about Level 3 causes electrified feeling even when the voltage can be varied on a scale of 10 levels (from Level 1 to Level 10), for example. Thus, a shock or pain may be given to the human body.

In this case, the frequency therapy device needs to be used without exceeding Level 1 or 2, or Level 3 for some individuals. Thus, voltages in the spike parts correspond to ⅓ or less of those obtained when the level is raised to Level 10. This makes the user feel that the pain relief effect is small. Similarly, it can be considered that there is an appropriate range also for a pulse width of the sharp-pointed top peak part.

Furthermore, after therapy for a single code number (which will be described later) is ended, a patient himself or herself, or his or her assistance needs to perform an operation of newly setting the next code number at the site of therapy. Thus, the process is complicated, and a blank time is inadvantageously created before setting the next code number.

CITATION LIST

Patent Literature

Patent Literature 1: U.S. Pat. No. 5,658,322

SUMMARY OF INVENTION

Technical Problem

An object of the present invention is to provide a frequency therapy device capable of recording with a digital waveform so that steep spike-shaped waveforms during a rise and a fall can be reliably regenerated in a waveform memory referred to as a so-called sound source chip, and capable of maintaining an impact given to a living body by a sharp-pointed top peak part or a sharp-pointed bottom peak part while reducing voltages (absolute values) in a high-level part following the spike-shaped sharp-pointed top peak part and a low-level part following the sharp-pointed bottom peak part, and capable of passing a current while giving very little pain to the patient's skin even in a low-frequency region.

Another object of the present invention is to provide a frequency therapy device having a low power consumption and suitable for use as a portable frequency therapy device.

A further object of the present invention is to provide a frequency therapy device having no need to set a code number for each therapy and thus placing less burden on a patient.

The present invention provides a frequency therapy device comprising: at least a pair of electrode pads capable of being in contact with a human body with an affected part being interposed therebetween; a main device unit that passes, between the pair of electrode pads, a current corresponding to a voltage waveform in which a direction thereof is reversed at regularly repeated time intervals and a voltage increases and decreases alternately on a positive side and a negative side; a display unit connected to the main device unit for displaying a magnitude of a voltage applied between the pair of electrode pads; and an operation/display panel for operating the main device unit, wherein the main device unit includes: a waveform memory that stores a plurality of voltage waveforms at different frequencies; and a central control unit configured to selectively read the plurality of voltage waveforms stored in the waveform memory, and repeatedly and successively use the read voltage waveform to pass a current between the pair of electrode pads, the waveform memory stores the voltage waveform, for each of the plurality of frequencies, as waveform data comprising a square wave with a sampling frequency of 192 kHz or higher and a number of quantization bits of 24 bits or more, and the central control unit is configured to read the waveform data from the waveform memory for each frequency, convert the waveform data to an analog waveform by a D/A converter during a preset time for the frequency, and pass a current corresponding to the voltage waveform between the pair of electrode pads; in a frequency range of at least 1000 Hz or lower, the waveform data stored in the waveform memory has, within a single waveform period, a waveform ranging from a rise portion heading toward a positive region from a 0-V level during a rise transition period, through a sharp-pointed top peak portion having a spike shape at an end of the rise and having a pulse width of 30 μsec to 200 μsec, a high-level portion in which the voltage is larger than 0 V and smaller than or equal to 5 V, a fall portion heading toward a negative region during a fall transition period, a sharp-pointed bottom peak portion having a spike shape at an end of the fall and having a pulse width of 30 μsec to 200 μsec, and a low-level portion in which the voltage is smaller than 0 V and larger than or equal to −5 V, to a next rise portion.

According to the present invention, spike part, i.e., part of a spike-shaped waveform, are referred to as the sharp-pointed top peak part and the sharp-pointed bottom peak part. "Frequencies" are defined to include low frequencies from 1 to 1000 Hz, medium frequencies from 1000 to 10000 Hz, and high frequencies, which are said to be 10000 Hz or higher but not clearly defined. The frequency therapy device according to the present invention, however, involves frequencies from 1 Hz to a high frequency of up to 30000 Hz, which is considered to have influence on the human body. The numerical values of a sampling frequency of 192 kHz and a number of quantization bits of 24 bits come from the numerical values of an existing, commercialized high-resolution uncompressed sound source. The present invention also encompasses cases with sound source waveforms having numerical values exceeding the aforementioned numerical values.

Advantageous Effects of Invention

The frequency therapy device according to the present invention provides the advantageous effects that the spike part during the rise and the spike part during the fall in the voltage waveform to be applied between the electrode pads can be accurately regenerated at the same frequency and successively, and a shock on the human body at portions where the electrode pads are attached can be reduced and a power consumption can be significantly reduced by setting voltage values between the spike parts to a range of 0 to ±5 V.

DESCRIPTION OF EMBODIMENTS

Embodiments of the present invention will be described below in detail with reference to the drawings.

First Embodiment

Figure 1:
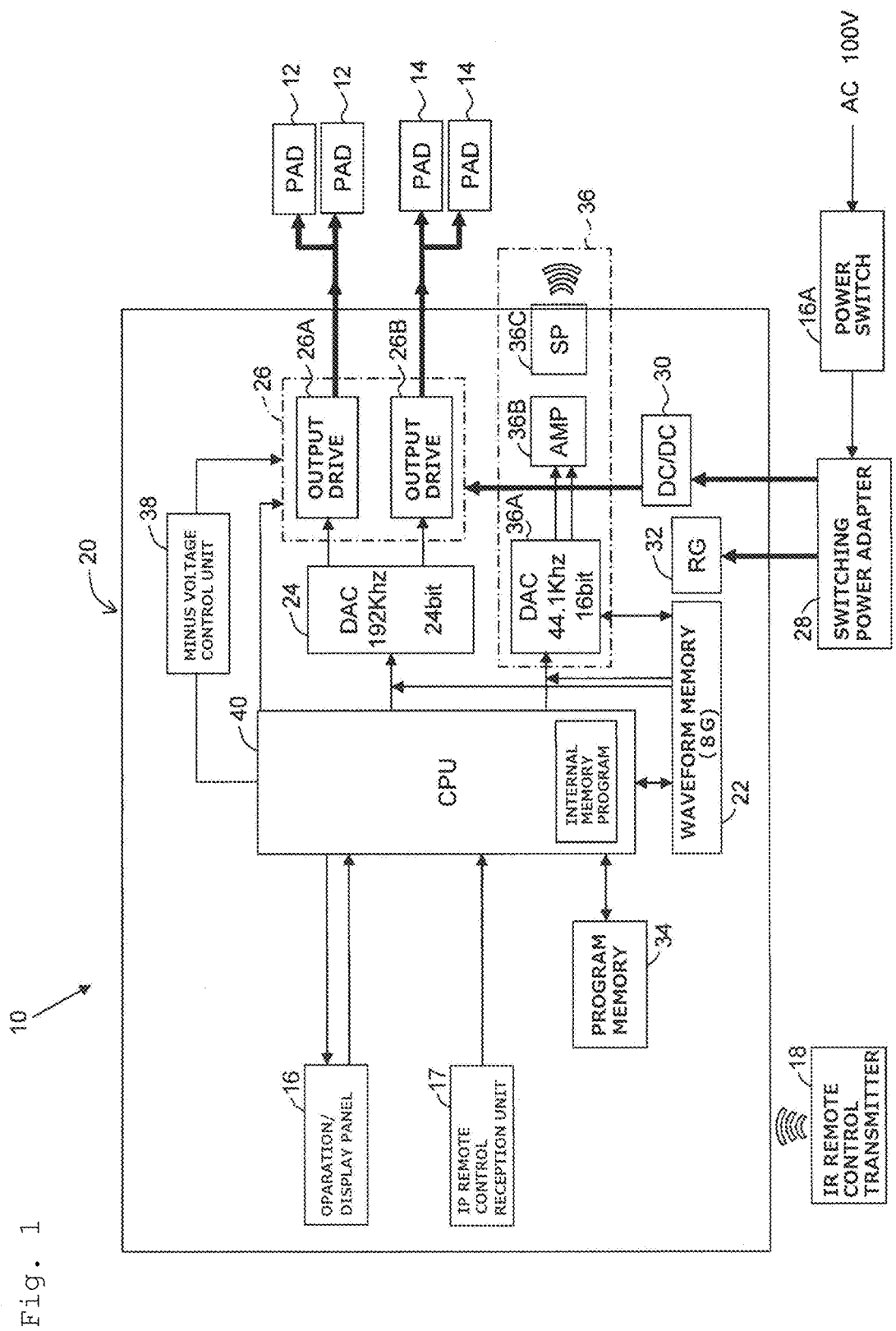
FIG. 1 is a block diagram showing a frequency therapy device according to a first embodiment of the present invention.
Figure 2:
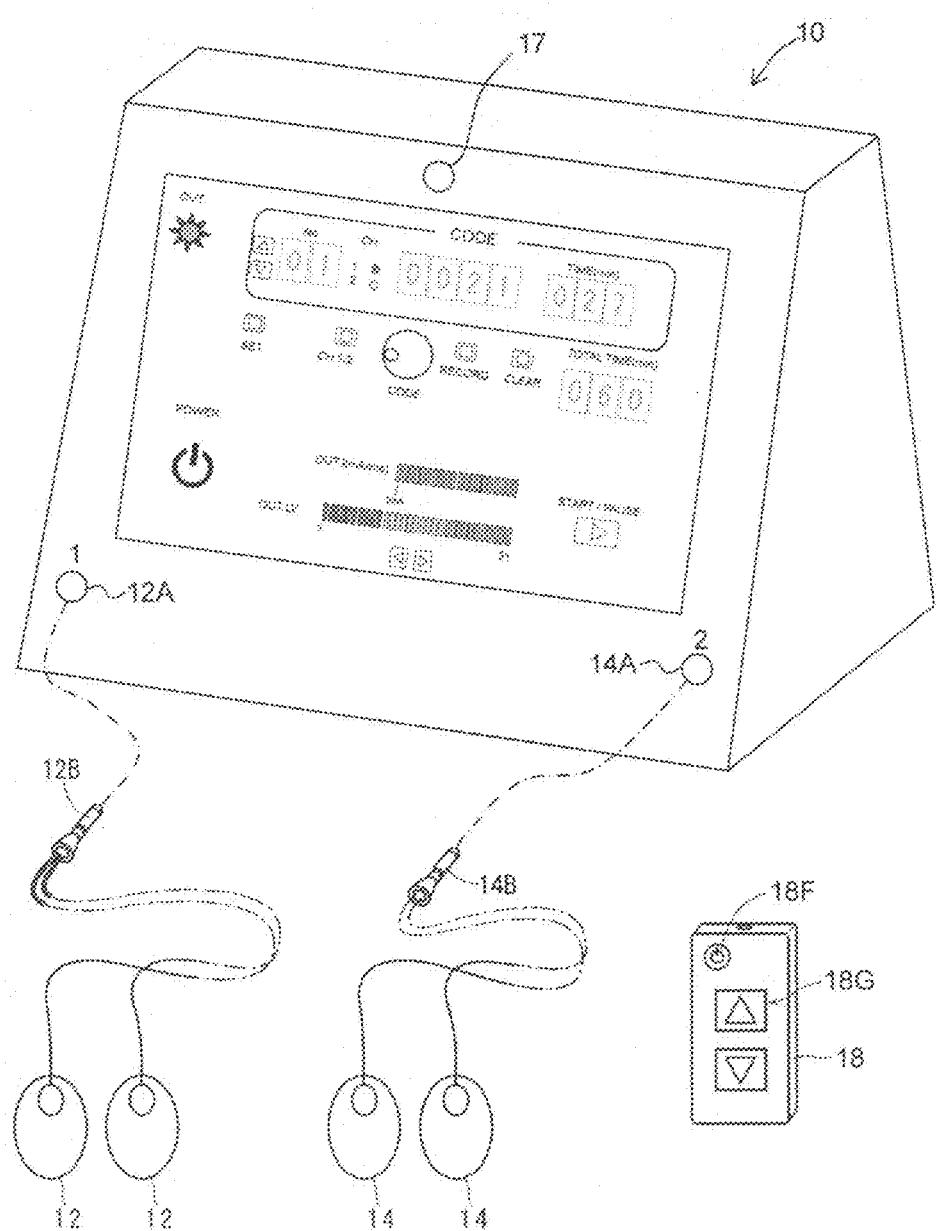
FIG. 2 is a perspective view showing an external appearance of the frequency therapy device.

As shown in FIG. 1 (a block diagram) and FIG. 2 (a perspective view showing an external appearance), a frequency therapy device 10 according to a first embodiment of the present invention is configured to include: two pairs of electrode pads 12, 12 and 14, 14, each pair being capable of being in contact with the human body with an affected portion being interposed therebetween; a main device unit 20 that passes, between the pair of electrode pads 12, 12 and/or between the pair of electrode pads 14, 14 (hereinafter, referred to as "between the electrode pads 12" for short), a current corresponding to a voltage waveform in which the direction thereof is reversed at regularly repeated time intervals and a voltage increases and decreases alternately on a positive side and a negative side; an operation/display panel 16 connected to the main device unit 20 for operating the main device unit 20 and providing various kinds of display; an IR remote control reception unit 17 that performs infrared transmission and reception, for example; an IR remote control transmitter 18 for transmitting an operation signal to the IR remote control reception unit 17; and a switching power adapter 28 for rectifying a 100 VAC input, which is inputted via a power switch 16A included in the operation/display panel 16, and outputting the rectified current to the main device unit 20.

Figure 3:
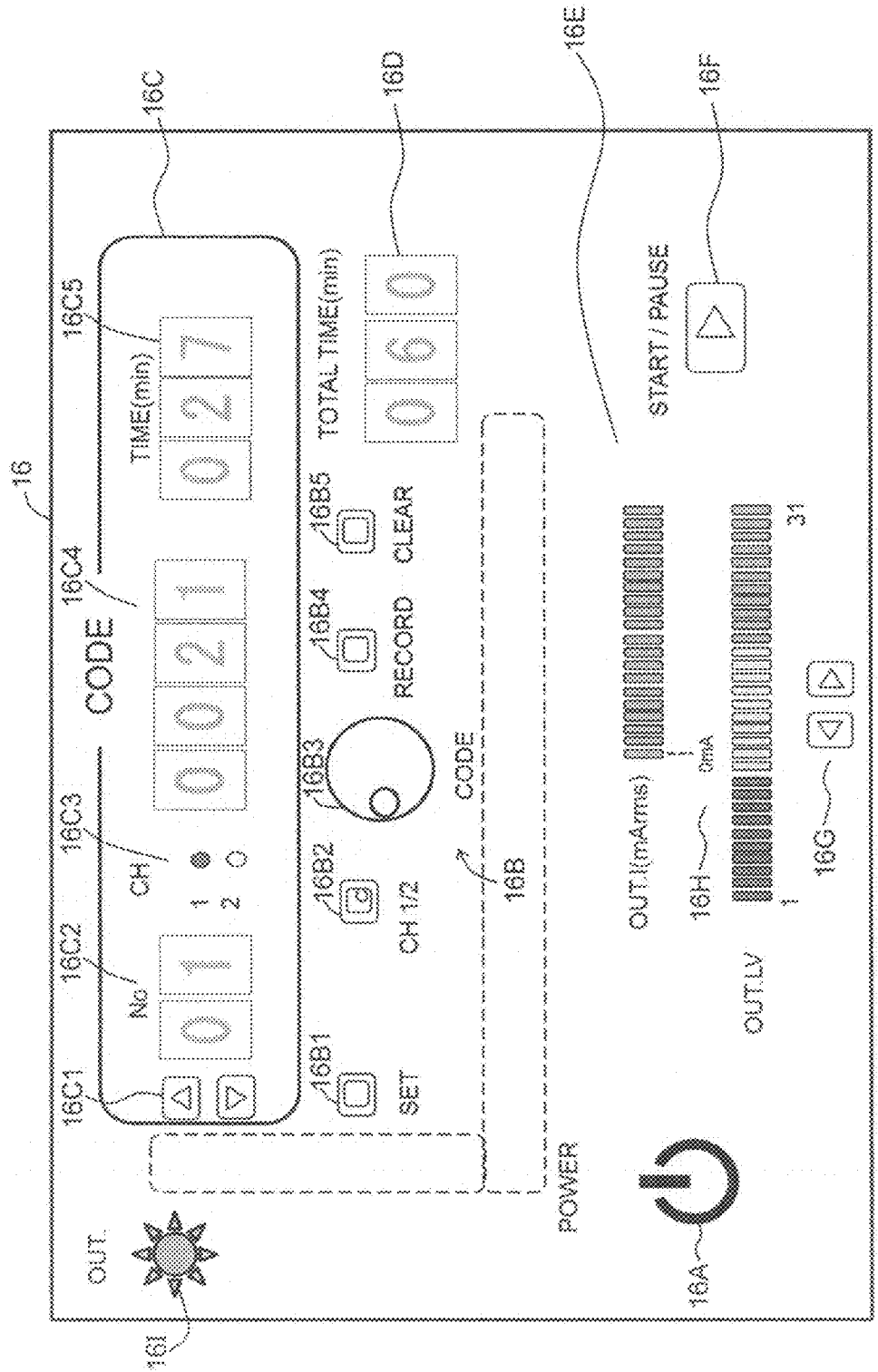
FIG. 3 is a front view showing an operation/display panel of the frequency therapy device.

As shown in FIG. 3 in detail, the operation/display panel 16 includes: the power switch 16A; a group 16B of setting switches; a code information display unit 16C; a remaining therapy time display unit 16D that displays, before therapy and during a setting operation, a total time of set code numbers and displays, during therapy, a remaining time of the therapy in a blinking manner; a current display unit 16E that displays a current level during therapy; a START/PAUSE switch 16F for starting/pausing/resuming therapy;

an output increase or decrease switch 16G for increasing or decreasing an output level during therapy; an output display unit 16H that displays 32 levels from 0 to 31 (0=OFF) by means of bar representation, for example; and an LED 161 for indicating that an output power (OUT) is on, which has a yellow color, for example.

The group 16B of setting switches includes: a SET switch 16B1 for setting a set value; an output channel (CH) selection switch 16B2 for selecting an output CH; a code setting dial 16B3 for setting a code value; a RECORD switch 16B4 for storing a setting; and a CLEAR switch 16B5 that, when being held down for three seconds or more, for example, deletes all of set codes before therapy and deletes the current code during a change.

The code information display unit 16C includes: a number up-down switch 16C1 for selecting a code number; a code number display unit 16C2 that displays, before therapy, code numbers from 1 to 11, for example, which have been selected by the number up-down switch 16C1, and displays, during therapy, a code number of the current therapy; an output CH display unit 16C3 that displays, before therapy, a CH setting for a number selected by the number up-down switch 16C1, displays, during a change, an output CH selected by the output channel selection switch 16B2 (the both are lit in the case of the CH 1 and the CH 2 at the same time, and the CH 1 and the CH 2 are both unlit in the case of an unregistered code "_____"), and displays, during therapy, the selected CH of the current code number; a code value display unit 16C4 that displays the code value of a number selected by the number up-down switch 16C1; and a code time display unit 16C5 that displays, before therapy, a code time registered for each number by the number up-down switch 16C1 in minutes, for example, displays, during a code change, a time registered in a code set by the code setting dial 16B3, and displays, during therapy, a remaining time of the code of the current therapy, for example, in a blinking manner.

Alternatively, the entire operation/display panel 16 may be configured as a single liquid crystal touch panel, for example.

As shown in FIG. 1, the main device unit 20 includes: a waveform memory 22 that stores a plurality of voltage waveforms at different frequencies; and a central control unit (hereinafter, referred to as a CPU) 40 that is configured to sequentially read the plurality of voltage waveforms stored in the waveform memory 22 and pass a current corresponding to the read voltage waveform between the pair of electrode pads 12, 12.

The waveform memory 22 is what is called a sound source memory, and stores a voltage waveform, for each of a plurality of frequencies, as waveform data formed with a sampling frequency of 192 kHz or higher and a number of quantization bits of 24 bits or more (which will be described later in detail).

The CPU 40 is configured to read waveform data from the waveform memory 22 for each frequency, output the waveform data to a D/A converter 24 so as to be converted to an analog waveform during a preset time for the frequency, and pass a current corresponding to the voltage waveform between the electrode pads 12, 12.

In addition to the waveform memory 22 and the D/A converter 24 described above, the main device unit 20 includes: an output drive set 26 including a pair of output drives 26A and 26B; a DC/DC converter 30; a regulator 32; a notification sound output system 36; and a minus voltage control unit 38.

The D/A converter 24 is configured to perform a digital-analog conversion on the waveform data read from the waveform memory 22 by the CPU 40 with a sampling frequency of 192 kHz or higher and a number of quantization bits of 24 bits or more and output the waveform data to the output drives 26A and 26B in an analog waveform.

The output drives 26A and 26B are configured to change the outputs from the D/A converter 24 on the basis of the aforementioned analog waveform and output the changed data to the electrode pads 12, 12 and the electrode pads 14, 14, respectively.

The CPU 40 is configured to be able to output, to the output drives 26A and 26B, a command signal to enable a mode in which the output drives 26A and 26B are activated simultaneously, a mode in which after the activation of one of the output drives 26A and 26B is ended, the other one of the output drives 26A and 26B is successively activated, or a mode in which the other one of the output drives 26A and 26B is continuously activated by repeating for a set number of times under the same code in accordance with the setting of the output CH selection switch 16B2 of the operation/display panel 16.

The DC/DC converter 30 is configured to step down a direct-current output from the switching power adapter 28 to a predetermined voltage, and the regulator 32 is configured to turn off the direct-current output when the output voltage and current from the switching power adapter 28 unusually increase.

A program memory 34 stores therein a program for operating the CPU 40. The notification sound output system 36 plays, for example, start-up sound when the power is turned on, therapy starting sound at the start of therapy, therapy ending sound at the end of therapy, error sound at the occurrence of an error (overcurrent, when started without the registration of a code, and the like), output level operation sound at the time of operating an output level, and the like. Specifically, the notification sound output system 36 is configured to provide information to be notified, such as "Ended" or "Will be paused," from a loudspeaker 36C by voice when a condition to be notified to a patient occurs, including the end of therapy.

Such voice information is set in an extra storage region 22-A (see FIG. 4) in the waveform memory 22. When a condition to be notified occurs, the voice information is sent from the waveform memory 22 to a D/A converter 36A in the notification sound output system 36 on the basis of an instruction signal from the CPU 40, converted to an analog signal in the D/A converter 36A, amplified by an amplifier 36B, and outputted as voice from the loudspeaker 36C.

As will be described later, the minus voltage control unit 38 displaces the 0-V level in a voltage waveform toward the plus side by 5% to 10% of the maximum voltage from the intermediate position in the waveform chart so that an amount of electrons entering the human body through the electrode pads 12, 12 becomes greater than an amount of electrons escaping from the body. In this manner, the minus voltage control unit 38 prevents the effects of deficiency in electrons on the human body. Here, the reason for being set to 5% or more is because deficiency in electrons in the human body can be prevented from occurring even when a source voltage fluctuates. The reason for being set to 10% or less is to prevent surplus in electrons.

As shown in FIG. 2, the IR remote control transmitter 18 is provided with a remote control START/PAUSE switch 18F, which is similar to the START/PAUSE switch 16F, and a remote control output increase or decrease switch 18G, which is similar to the output increase or decrease switch 16G. The IR remote control transmitter 18 is provided for each output CH (in the case of two channels, two IR remote control transmitters 18 are provided in total). Note that the remote control is not limited to an infrared remote control.

The reference numerals 12A and 14A in FIG. 2 denote jacks for receiving plugs 12B and 14B of the electrode pads 12 and 14. The jacks 12A and 14A constitute a first output channel and a second output channel, respectively.

A configuration of the CPU 40 and the waveform memory 22 will be described next.

Figure 4:
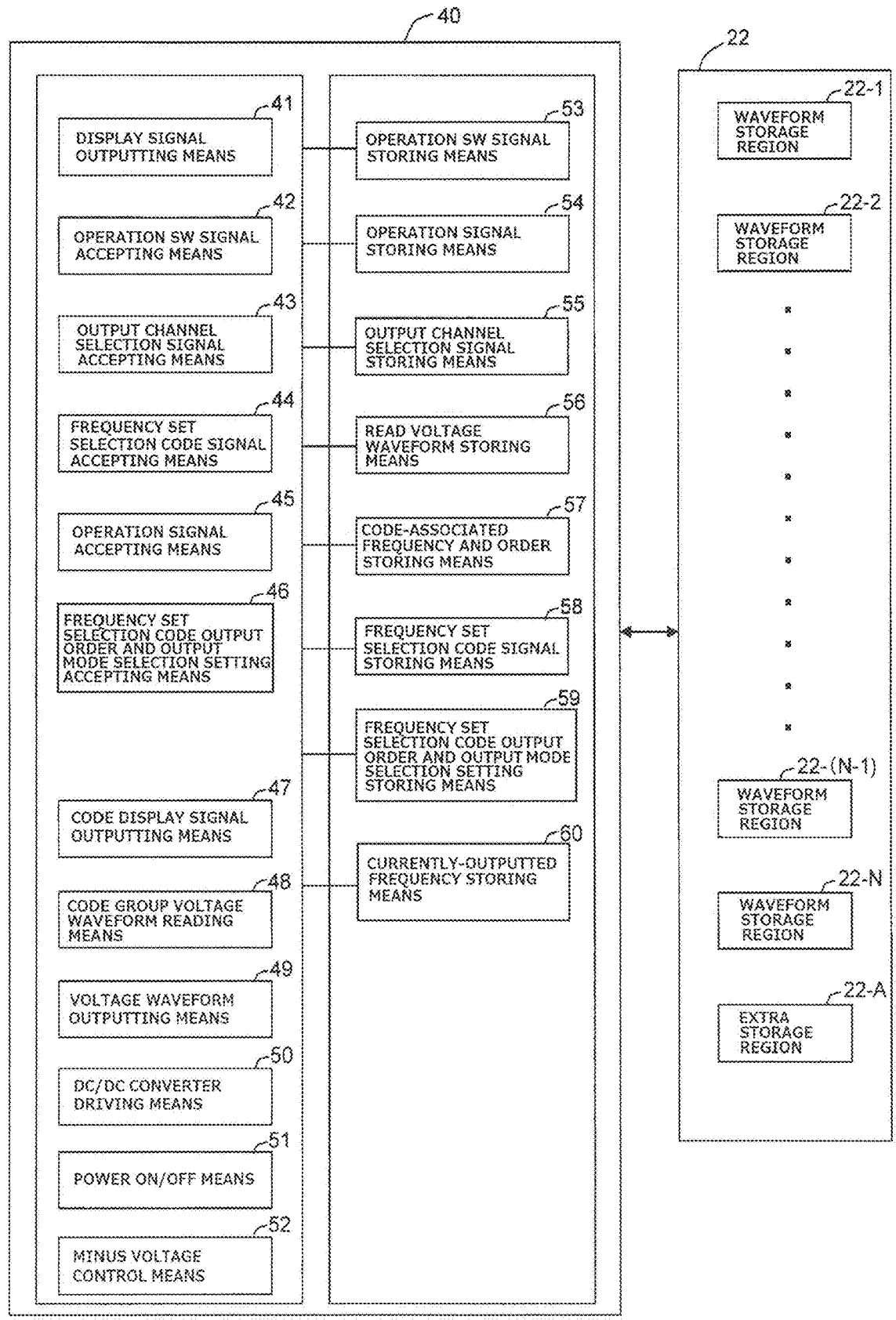
FIG. 4 is a block diagram showing general configurations of a central control unit and a waveform memory in the frequency therapy device.

As shown in FIG. 4, the CPU 40 is configured to include: a display signal outputting means 41; an operation switch signal accepting means 42; an output channel selection signal accepting means 43; a frequency set selection code signal accepting means 44; an operation signal accepting means 45; a frequency set selection code output order and output mode (one of the pair, alternately, or simultaneously) selection setting accepting means 46; a code display signal outputting means 47; a code group voltage waveform reading means 48; a voltage waveform outputting means 49; a DC/DC converter driving means 50; a power ON/OFF means 51; a minus voltage control means 52; an operation switch signal storing means 53; an operation signal storing means 54; an output channel selection signal storing means 55; a read voltage waveform storing means 56; a code-associated frequency and order storing means 57; a frequency set selection code signal storing means 58; a frequency set selection code output order and output mode (one of the pair, alternately, or simultaneously) selection setting storing means 59; and a currently-outputted frequency storing means 60.

The display signal outputting means 41 is configured to display, at the output display unit 16H and the code number display unit 16C2, output intensity and a code number operated by the output increase or decrease switch 16G and the number up-down switch 16C1 in the operation/display panel 16. The output channel selection switch 16B2 itself is made as a touch panel. Each touch alternately displays a number from "1" to "2" and from "2" to "1."

The operation switch signal accepting means 42 is configured to accept operation signals from the group 16B of setting switches in the operation/display panel 16. Moreover, the accepted signals are stored in the operation switch signal storing means 53.

The operation signal accepting means 45 is configured to accept operation signals transmitted from the operation/display panel 16 and the IR remote control transmitter 18. The accepted operation signals, specifically, an output intensity signal and a code number signal to be described later, are stored in the operation signal storing means 54.

The output channel selection signal accepting means 43 is configured to accept an output channel selection signal determined by an operation of the output CH selection switch 16B2, and this signal is stored in the output channel selection signal storing means 55.

The code display signal outputting means 47 is configured to display information of an inputted code number at the code information display unit 16C on the basis of a display signal stored in the operation switch signal storing means 53.

The code-associated frequency and order storing means 57 stores, corresponding to a code, a plurality of frequencies predefined, for each code, to be included in the code and their output order. As shown in Table 1, for example, a frequency set selection code and the first to the n-th frequencies (n is a natural number greater than or equal to two) are stored in combination. Specifically, for the code number 1231, 20 Hz, 880 Hz, 5 kHz, . . . , 10 kHz are stored in this order.

TABLE 1

| CODE NUMBER | FIRST FREQUENCY | SECOND FREQUENCY | THIRD FREQUENCY | n-TH FREQUENCY |
|---|---|---|---|---|
| 1231 | 20 Hz | 880 Hz | 5 kHz | 10 kHz |
| 1232 | 60 Hz | 125 Hz | 2128 Hz | 5 kHz |
| 1467 | 72 Hz | 660 Hz | 2000 Hz | 10 kHz |
| . | . | . | . | |
| . | . | . | . | |
| . | . | . | . | |

The frequency set selection code output order and output mode selection setting accepting means 46 is configured to accept selection settings for frequency set selection code output order and output mode (one of the pair, alternately, or simultaneously) by the set order of the code setting dial 16B3 and an operation of the output CH selection switch 16B2, and this signal is stored in the frequency set selection code output order and output mode selection setting storing means 59.

On the basis of an inputted code signal and information stored in the code-associated frequency and order storing means 57 and the frequency set selection code output order and output mode selection setting storing means 59, the code group voltage waveform reading means 48 is configured to sequentially read, from the waveform memory 22, the voltage waveforms at the plurality of frequencies included in the code in accordance with the output order and the output mode (one of the pair, alternately, or simultaneously) stored in the read voltage waveform storing means 56.

The voltage waveform outputting means 49 is configured to output, to the D/A converter 24, data on the voltage waveforms at the frequencies read by the code group voltage waveform reading means 48.

The DC/DC converter driving means 50 is configured to drive the DC/DC converter 30 in accordance with the output intensity operated by the output increase or decrease switch 16G.

The power ON/OFF means 51 is configured to turn on or off a 100 VAC input to the switching power adapter 28 in accordance with an operation of the power switch 16A.

The currently-outputted frequency storing means 60 is configured to store the frequency of the waveform data being currently outputted from the voltage waveform outputting means 49.

The operation switch signal accepting means 42 is configured to turn off the DC/DC converter 30 by the regulator 32 so as to interrupt current supply from the output drive set 26 when an interruption signal for interrupting therapy is inputted by an operation of the remote control START/PAUSE switch 18F in the IR remote control transmitter 18 during therapy provided by the frequency therapy device 10.

The code group voltage waveform reading means 48 in this case is configured to read frequency information at the time of the interruption, which has been stored in the currently-outputted frequency storing means 60, and read the voltage waveform at that frequency when the therapy is resumed.

The waveform memory 22 includes N (N is a natural number greater than or equal to two) waveform storage regions 22-1 to 22-N, and the number of therapy frequencies used in the frequency therapy device 10 in this embodiment is N. Voltage waveforms at the N frequencies are stored in any of the waveform storage regions 22-1 to 22-N for each frequency.

Figure 5:
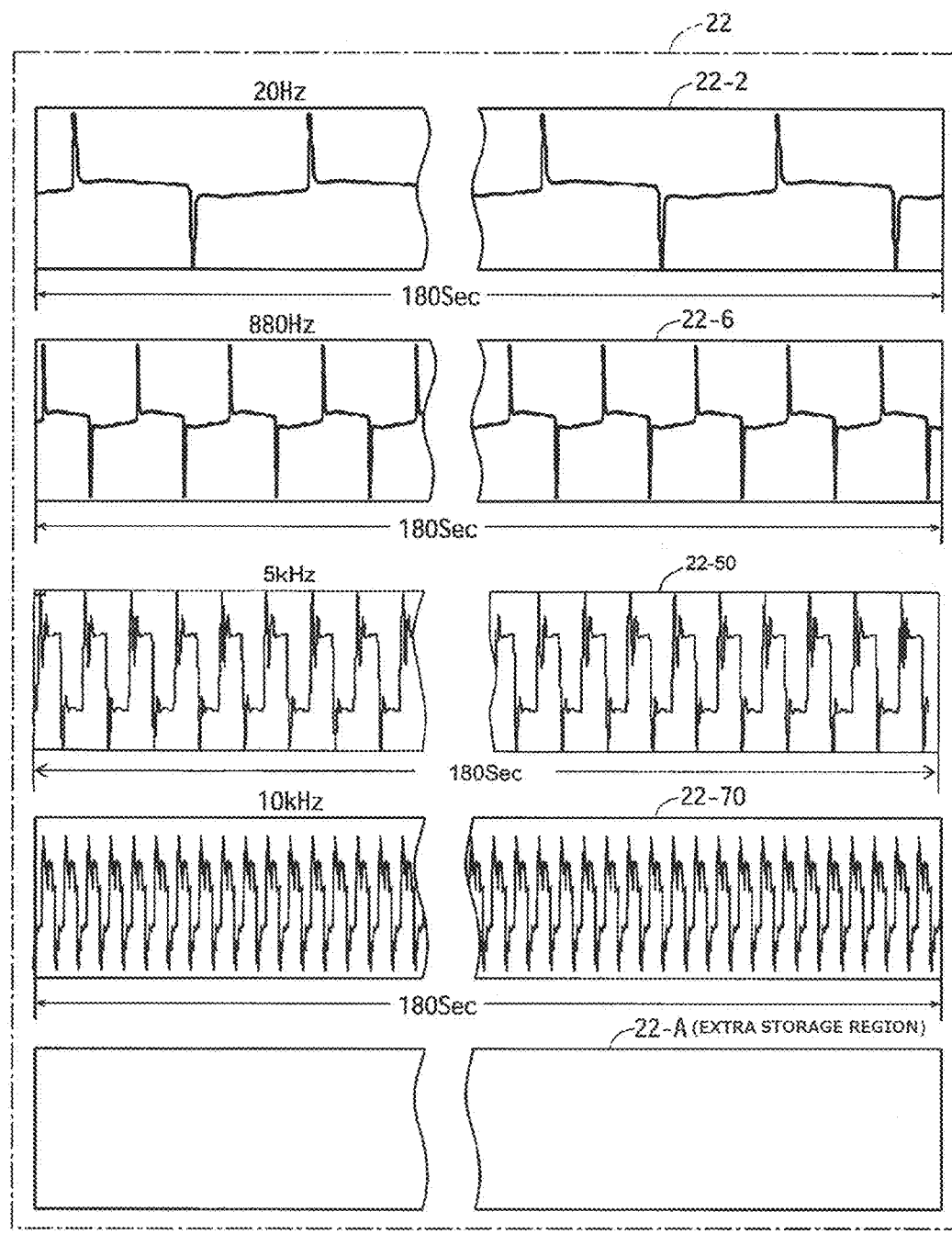
FIG. 5 is a chart showing an example of voltage waveforms stored in the waveform memory.

FIG. 5 shows an example of recorded states of voltage waveforms in the waveform storage regions of the waveform memory 22. FIG. 5 schematically shows the states of the voltage waveforms, in the case of the code number 1231, for example, at four frequencies of 20 Hz, 880 Hz, 5 kHz, and 10 kHz belonging to this code number.

In each of the waveform storage regions 22-1 to 22-N in the waveform memory 22, a voltage waveform at the same frequency and having the same waveform is successively and repeatedly stored for three minutes. In the case of a frequency of 20 Hz, for example, the same voltage waveform is repeatedly stored to have 3 (minutes)×60 (seconds)×20=3600 voltage waveforms in total. A distance between the voltage waveforms is constant, and there is no overlapping or separation between adjacent ones of the waveforms.

Figure 6:
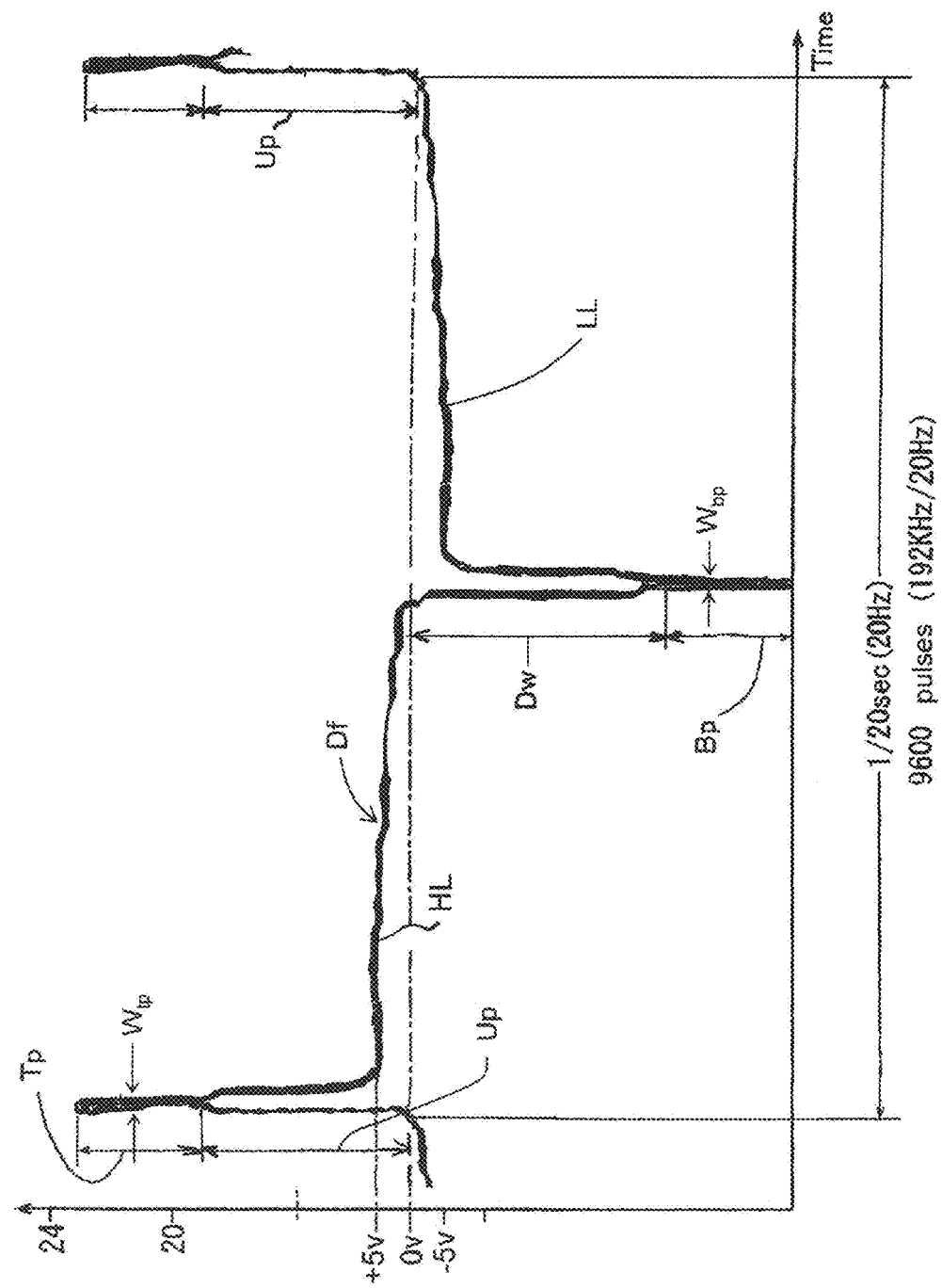
FIG. 6 is a chart showing a relationship between a sampling frequency and the number of quantization bits in a voltage waveform stored in the waveform memory.

Each voltage waveform is basically in a state as shown in FIG. 6, has a number of quantization bits of 24 bits or more and a sampling frequency of 192 kHz, and is formed by a digital signal divided into a time corresponding to the inverse of the sampling frequency. In the case of a frequency of 20 Hz, for example, a waveform for ½₀ second (the inverse of the frequency) is constituted of 192 kHz/20 Hz=9600 pulses.

A voltage in a high-level part HL and a voltage in a low-level part LL have a maximum value of +5 V and a minimum value of −5 V, respectively.

As shown in FIG. 6 in an enlarged manner, waveform data stored in each of the waveform storage regions in the waveform memory 22 has, within a single waveform period, a waveform Df ranging from a rise part Up heading toward a positive region during a rise transition period, through a sharp-pointed top peak part Tp having a spike shape at the end of the rise, the high-level part HL having a smaller value than that of the sharp-pointed top peak part Tp, a fall part Dw heading toward a negative region during a fall transition period, a sharp-pointed bottom peak part Bp having a spike shape at the end of the fall, and the low-level part LL having a larger value than that of the sharp-pointed bottom peak part Bp, to the next rise part Up.

A height (absolute value) between tips of the sharp-pointed top peak part Tp and the sharp-pointed bottom peak part Bp represents the maximum voltage, and each of a voltage at the sharp-pointed top peak part Tp and a voltage at the sharp-pointed bottom peak part Bp can be expressed by the maximum value corresponding to a number of quantization bits of 24 bits on a plus side or a minus side. In the waveform shown in FIG. 6, the sharp-pointed top peak part Tp and the sharp-pointed bottom peak part Bp corresponded to 35 V and −35 V, respectively, and the maximum voltage was |+35|+|'35|=70 V. Each of the maximum pulse widths $W_{tp}$ and $W_{bp}$ of the sharp-pointed top peak part Tp and the sharp-pointed bottom peak part Bp was about 110 μsec.

Here, the pulse widths $W_{tp}$ and $W_{bp}$ of the sharp-pointed top peak part Tp and the sharp-pointed bottom peak part Bp in the above-described waveform Df are defined to be 30 μsec to 200 μsec in a frequency range of 1000 Hz or lower. The reason for being set to 30 μsec or more is because a pulse width smaller than 30 μsec results in a very small pain relief effect or gives a patient no sense of undergoing therapy, for example.

For a maximum width of 300 μsec, for example, an impact given to a patient became strong, thereby causing a sense of discomfort.

In terms of a relationship with a frequency, a wavelength time for one waveform is 0.001 sec=1000 μsec in the case of 1000 Hz, for example. Of 1000 μsec, 300 μsec×2=600 μsec corresponds to the pulse widths $W_{tp}$ and $W_{bp}$ of the sharp-pointed top peak part Tp and the sharp-pointed bottom peak part Bp. Thus, a pulse width of the part of 0 to 5 V between the sharp-pointed top peak part Tp and the sharp-pointed bottom peak part Bp becomes smaller than the sharp-pointed top peak part Tp and the sharp-pointed bottom peak part Bp. This reduces the effect of reducing power consumption and also reduces the effect of giving an accurate impact on an affected part by the sharp-pointed top peak part Tp and the sharp-pointed bottom peak part Bp.

When each of the pulse widths $W_{tp}$ and $W_{bp}$ of the sharp-pointed top peak part Tp and the sharp-pointed bottom peak part Bp is set to 60 μsec or less, the above-described effect of reducing power consumption can be obtained over 1000 Hz and even up to 2000 Hz.

Moreover, the CPU 40 is configured so that two different frequency set selection codes can be inputted via the frequency set selection code signal accepting means 44 by switching the output CH selection switch 16B2 in the operation/display panel 16, and such a frequency set selection code is stored in the frequency set selection code signal storing means 58. Pieces of waveform data for a plurality of frequencies preset corresponding to an inputted frequency set selection code are sequentially read from the waveform storage regions 22-1 to 22-N of the waveform memory 22 that store the pieces of waveform data in a predefined order during a set time for each frequency, and then outputted.

Furthermore, the CPU 40 is configured to include the code-associated frequency and order storing means 57 that stores a frequency set selection code, frequencies corresponding to this frequency set selection code, and an output order of pieces of waveform data for these frequencies; the code group voltage waveform reading means 48 that reads, from the waveform memory 22, the pieces of waveform data for the frequencies in accordance with the order stored in the code-associated frequency and order storing means 57 and the frequency set selection code output order and output mode selection setting storing means 59; and the voltage waveform outputting means 49 that outputs the pieces of waveform data read by the code group voltage waveform reading means 48 in the aforementioned order.

Two output drive sets 26 are provided in the first embodiment. The CPU 40 is configured so that an output channel can be selected by the output CH selection switch 16B2; for each of the first and second output channels, a code different for each of the selected 11 code numbers from "01" to "11" can be set by the number up-down switch 16C1; and a direct current can be first supplied only to the output drive 26A, of the two output drives 26A and 26B, and a direct current can be supplied to the other output drive 26B only after the completion of the supply of the direct current by the output drive 26A, for example. Alternatively, an output can be provided alternately from the first output channel and the second output channel, outputs can be provided simultaneously to treat two persons, or two outputs outputted to a person can be caused to interfere with each other.

In the first embodiment, the output drive 26A of the first channel and the output drive 26B of the second channel are independent of each other to constitute fully parallel two channels. Thus, as compared to a case where a single channel is simply split into two channels, an increased amount of current flowing through one of the channels causes no reduced amount of current flowing through the other one of the channels. Moreover, currents corresponding to different codes can be caused to flow through the two channels.

Figure 7:
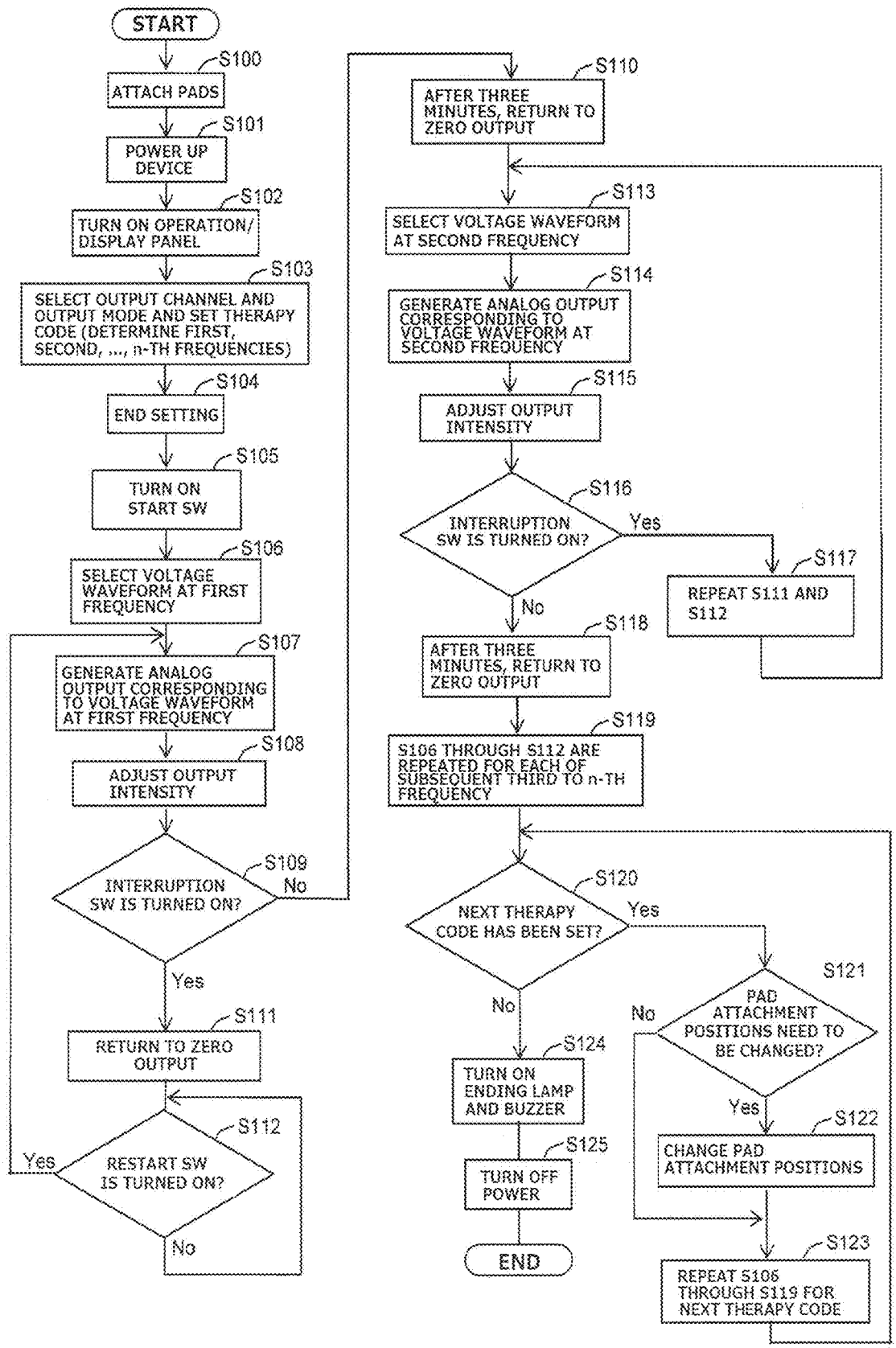
FIG. 7 is a flowchart showing a process of therapy performed by the frequency therapy device.

With reference to FIG. 7, a process of therapy performed by the frequency therapy device 10 of the above-described embodiment will be described next.

Figure 8A:
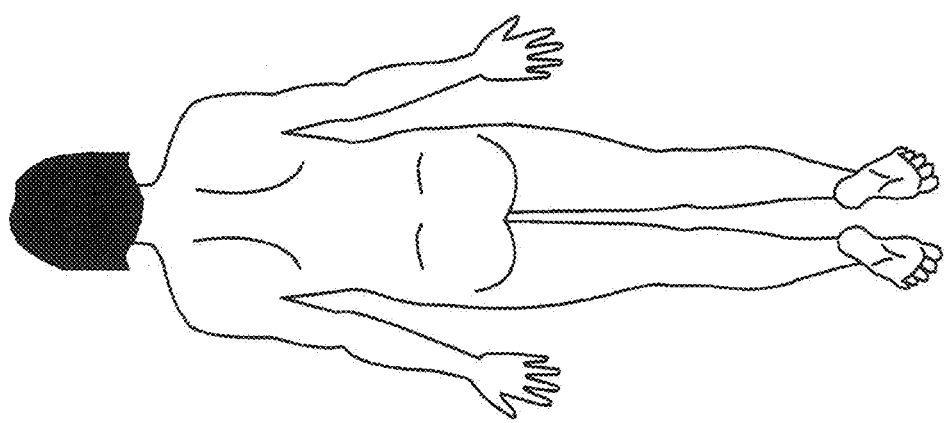
FIG. 8 is a diagram showing examples of pad attachment positions of the frequency therapy device.
Figure 8B:
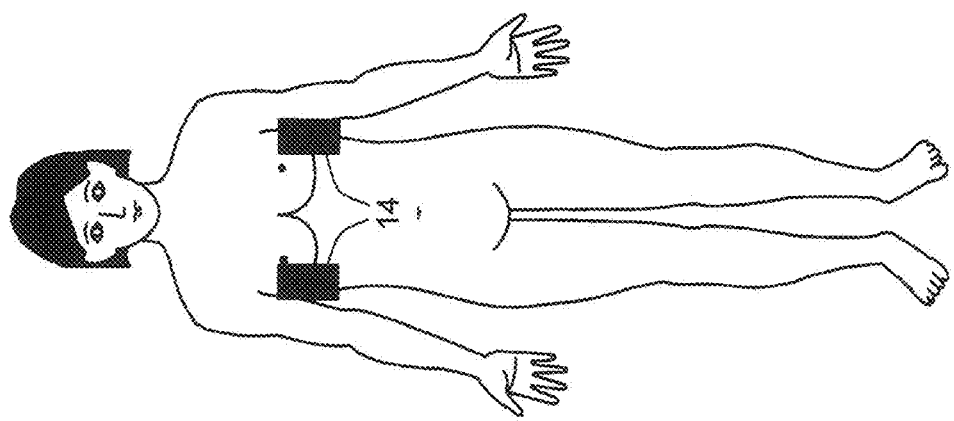

In step S100, the electrode pads 12 (or 14) are first attached to predetermined sites depending on a pain relief target as shown in FIG. 8 as an example. FIG. 8A shows an example in which the pair of electrode pads 12 are attached to the target right flank, and FIG. 8B shows an example in which the pair of electrode pads 14 are attached to the target right and left flanks. Note that the positions of the electrode pads 12 and 14 are not limited to the above positions, but may be the soles of the feet, for example.

To start therapy, the power switch 16A is first turned on in step S101 to power up the device. After the respective parts are all lit by lighting all LEDs once, pieces of code information (a code, a time, an output CH, and a therapy time) are displayed. The pieces of code information are the same as the previous settings before the power is turned off. At the same time, start-up sound is emitted.

Next, in step S102, the operation/display panel 16 is turned on to obtain a state in which a therapy code can be set by the group 16B of setting switches.

In step S103, the output drives 26A and 26B are sequentially selected and an output mode is selected by operations of the output channel selection switch 16B2. Thereafter, for each of the selected codes, a four-digit therapy code is set by the code setting dial 16B3 while viewing the code value display unit 16C4 (a therapy code may be set only for the output drive 26A).

In the following step S104, the setting is registered by the RECORD switch 16B4, and the change is ended. This activates the code group voltage waveform reading means 48, thereby obtaining a state in which data on a waveform for each frequency can be sequentially read, as a voltage waveform at the first, second, . . . , or n-th frequency, on the basis of a signal from the code-associated frequency and order storing means 57, from any of the waveform storage regions 22-1 to 22-N in the waveform memory 22 in accordance with the stored order.

A case where the set code is changed is shown in FIG. 9 as an example. The eleven code numbers from 01 to 11 can be set.

Figure 9A:
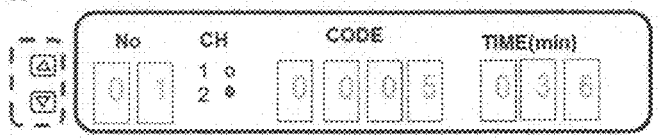
FIG. 9 is a front view showing display examples of the operation panel when a code is changed in the frequency therapy device.

First, as shown in FIG. 9A, the current code information (in the figure, a code number of 01, an output CH of 2, a code value of 0005, and a time of 036 minutes used in the previous therapy, for example) is still shown and this information is checked. If there is no need to change the information, setting for the next code number 02 is started.

Figure 9B:
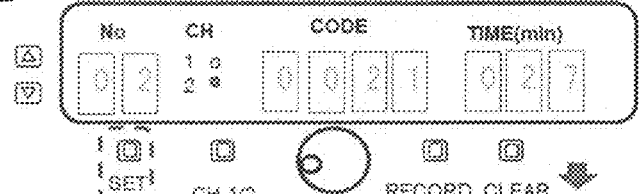

First, the code number is changed by the number up-down switch 16C1. In FIG. 9B, while the code number is changed from 01 to 02, an output CH of CH 2, a code value of 0021, and a time of 027 used in the previous therapy are still shown.

Figure 9C:
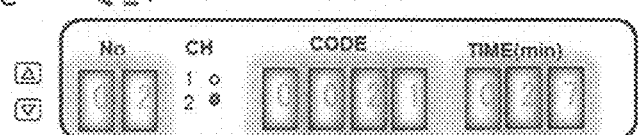

Next, as shown in FIG. 9C, pressing the SET switch 16B1 causes the LEDs of NO, CODE, and TIME, and the output CH display unit 16C3 to blink, and a state in which a change can be made is obtained. At this time, the code value is changed by turning the code setting dial 16B3.

Figure 9D:
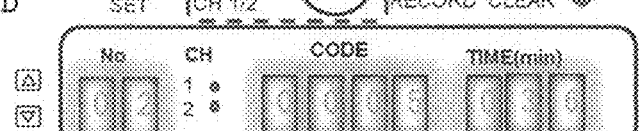

Next, the output CH is changed (the CH 1 or the CH 2, or the CH 1 and the CH 2 at the same time) by the output CH selection switch 16B2 as shown in FIG. 9D. FIG. 9D shows an example in which the code value has been changed to "0005" and the output CH has been set to the CH 1 and the CH 2 at the same time. Since a time and a code value are defined as a set, "036" corresponding to "0005" is displayed.

Figure 9E:
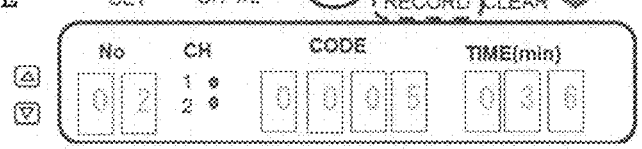

Next, as shown in FIG. 9E, the RECORD switch 16B4 is pressed to register the settings. This changes the blinking state to a lit state, and ends the change.

Next, a case where a code number of 03 is selected and an unregistered code that has not been previously used is set will be shown in FIG. 10.

Figure 10A:
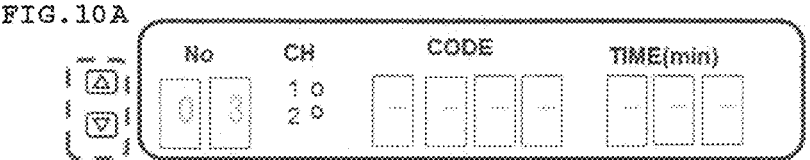
FIG. 10 is a front view similarly showing display examples of the operation panel when a code is newly registered.

First, an unregistered number is displayed as " - - - - " as shown in FIG. 10A. At this time, pressing the SET switch 16B1 results in a state in which a change can be made. Registration is performed by the same operations as those at the time of the aforementioned change.

Figure 10B:
Figure 10B:
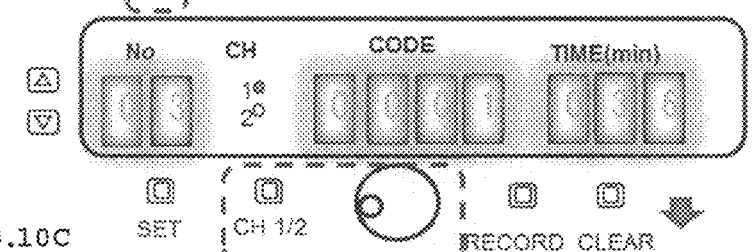

More specifically, the code value is changed by the code setting dial 16B3, and the CH output is changed (the CH 1 or the CH 2, or the CH 1 and the CH 2 at the same time) by the output CH selection switch 16B2 as shown in FIG. 10B.

Figure 10C:
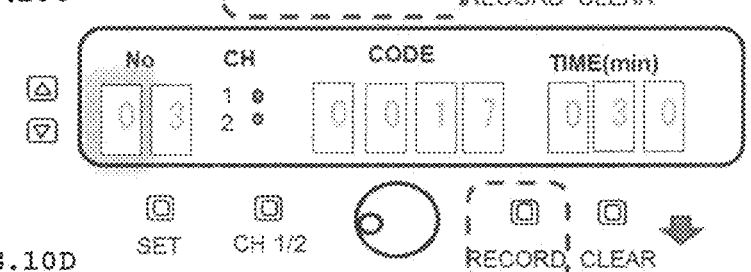

FIG. 10C shows an example in which the code value "0017" has been registered, and the output CH has been set to the CH1 and the CH2 at the same time.

Figure 10D:
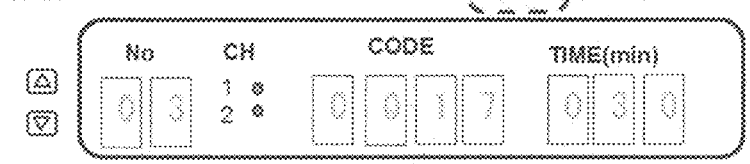

Next, as shown in FIG. 10D, the RECORD switch 16B4 is pressed to register the settings. This changes the blinking state to the lit state, and ends the registration.

A case where the registration of a single target code is deleted is shown in FIG. 11.

Figure 11A:
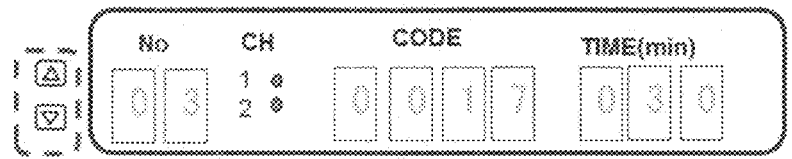
FIG. 11 is a front view similarly showing display examples of the operation panel when a target code is deleted.

In this case, a code number (e.g., "03") the user wishes to delete is selected by the number up-down switch 16C1, and then the SET switch 16B1 is pressed to obtain a state in which a change can be made as shown in FIG. 11A.

Figure 11B:
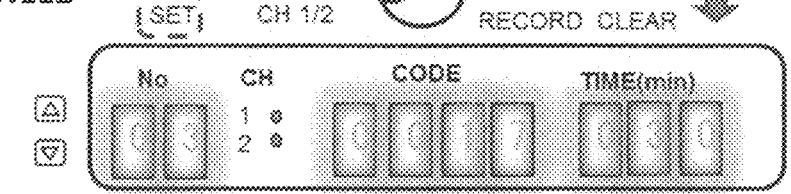

Next, in the state in which a change can be made (blinking), the CLEAR switch 16B5 is held down for three seconds, for example, to cancel the registration as shown in FIG. 11B.

Figure 11C:
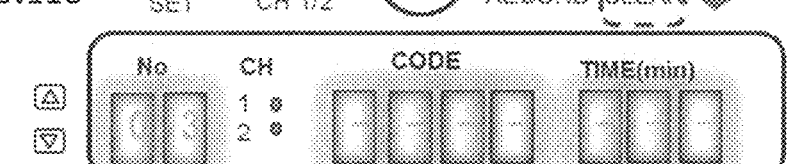

Next, the RECORD switch 16B4 is pressed to register the setting and the deletion is ended as shown in FIG. 11C.

Figure 11D:
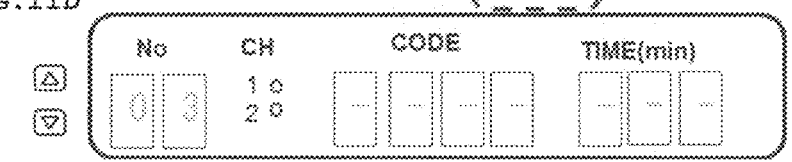

The end state is shown in FIG. 11D. A new code can be immediately inputted by the code setting dial 16B3.

A case where the registration of all codes is deleted at once, as in a case where codes are newly inputted from scratch, is shown in FIG. 12.

Figure 12A:
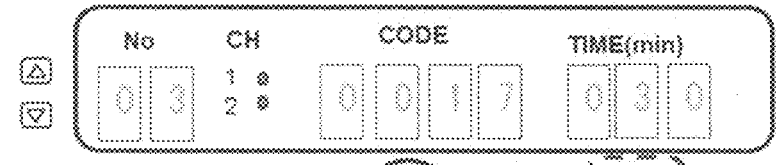
FIG. 12 is a front view similarly showing display examples of the operation panel when all codes are deleted at once.

In this case, the CLEAR switch 16B5 is held down for three seconds, for example, to cancel the registrations as shown in FIG. 12A.

Figure 12B:
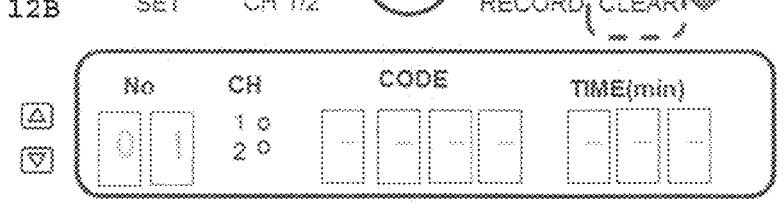

This cancels all of the registered codes as shown in FIG. 12B.

After the end of step S104 in FIG. 7, the START/PAUSE switch 16F is turned on in the following step S105. In the following step S106, the voltage waveform at the first frequency is selected, and the voltage waveform stored, for example, in the waveform storage region 22-2 of the waveform memory 22 is read. Since the voltage waveform for three minutes is successively stored in the waveform storage region 22-2, an analog output corresponding to the voltage waveform at the first frequency is generated from the output drive 26A in step S107.

Here, when the present output mode stored in the frequency set selection code output order and output mode selection setting storing means 59 is the output channel 2, the analog output is generated from the output drive 26B. When the alternate output mode is stored, the output is generated alternately from the output drives 26A and 26B. When the simultaneous output mode is stored, outputs are generated from both of the output drives 26A and 26B simultaneously. When the outputs are generated simultaneously, the outputs can be provided to two persons simultaneously, or the two outputs can be applied to a person simultaneously and the two outputs can be caused to interfere with each other by crossing, for example.

Immediately after a pulse is generated, output intensity indicated in the output display unit 16H of the operation/display panel 16 is adjusted in the following step S108 by an operation of the output increase or decrease switch 16G also included in the operation/display panel 16 to a level at which no pain is caused at the portions of the electrode pads that are in contact with the patient, for example.

The analog output corresponding to the voltage waveform at the first frequency continues for three minutes. To interrupt the therapy halfway due to some problem, however, the remote control START/PAUSE switch 18F is activated by the IR remote control transmitter 18, and such activation serves as an interruption switch. In step S109, "Yes" is selected, and the analog output returns to zero at step S111. At the same time, notification sound such as "Will be paused" is outputted from the loudspeaker 36C.

If no interruption switch is turned on during these three minutes, "No" is selected in step S109, and the process proceeds to step S110. After three minutes of the analog output generation time, the output returns to zero.

If the remote control START/PAUSE switch 18F is activated by the IR remote control transmitter 18 after the output is returned to zero by turning the interruption switch on, on the other hand, such activation serves to turn a restart switch on. In step S112, "Yes" is selected, and the process returns to step S107. If "No," the process returns to step S112.

After the end of step S110, the next voltage waveform at the second frequency is selected in the following step S113. In the following step S114, an analog output corresponding to the voltage waveform at the second frequency selected in step S113 is generated.

As with the case of the voltage waveform at the first frequency, output intensity is adjusted in step S115, and whether the interruption switch is turned on is determined in step S116. If "Yes," the process proceeds to step S117. After steps S111 and S112 are repeated, the process returns to step S113.

If the determination on whether the interruption switch is turned on is "No" in step S116, then the process proceeds to step S118 where the output returns to zero after three minutes of the generation of the analog output corresponding to the voltage waveform at the second frequency. In the following step S119, the above-described steps from S106 through S112 are repeated for each of the subsequent third to the n-th frequencies. After three minutes of the generation of the analog output for the n-th frequency, the process proceeds to step S120.

In step S120, whether the next therapy code has been set and stored in the frequency set selection code output order and output mode selection setting storing means 59 is determined. If "No," then the process proceeds to step S124 and an ending lamp and a buzzer are turned on. More specifically, the end of the therapy is notified to the patient from the loudspeaker 36C of the notification sound output system 36. The patient or his or her assistance then turns off the power switch 16A, thereby ending the process at step S125.

If the output of the next therapy code for the output drive 26B has been set and stored by the output CH selection switch 16B2, the determination result at step S120 is "Yes." Whether pad attachment positions need to be changed is determined in step S121. If the determination result is "Yes," the process proceeds to step S122 to change the pad attachment positions.

After the end of step S122, or if the determination result in step S121 is "No," then the process proceeds to step S123 to repeat the above-described steps from S106 through S119 for the next therapy code. After the end of those steps, the process returns to step S120.

Second Embodiment

A second embodiment of the present invention for a portable type will be described next in detail with reference to the drawings.

Figure 13:
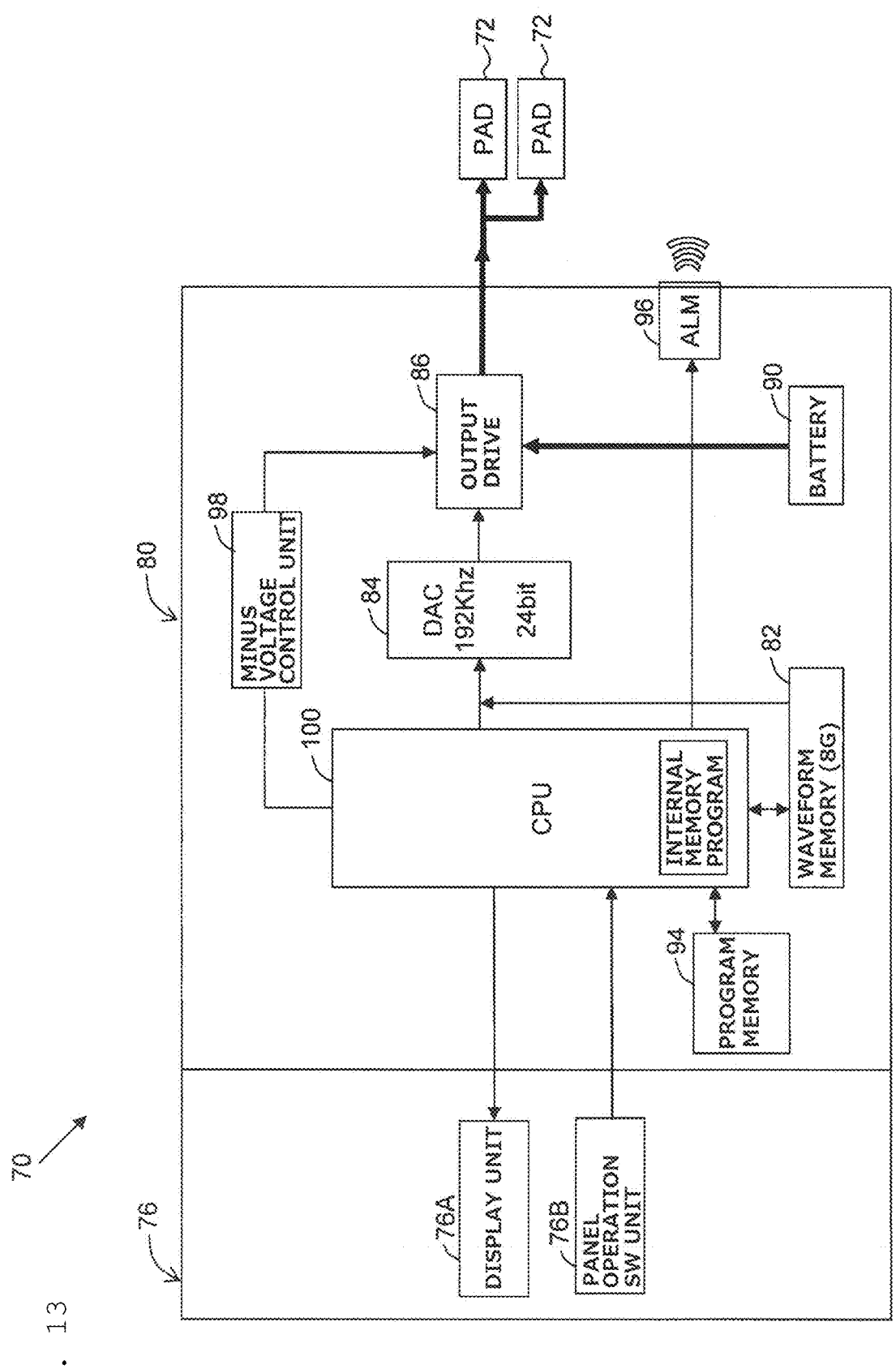
FIG. 13 is a plan view schematically showing a portable frequency therapy device according to a second embodiment of the present invention.
Figure 14:
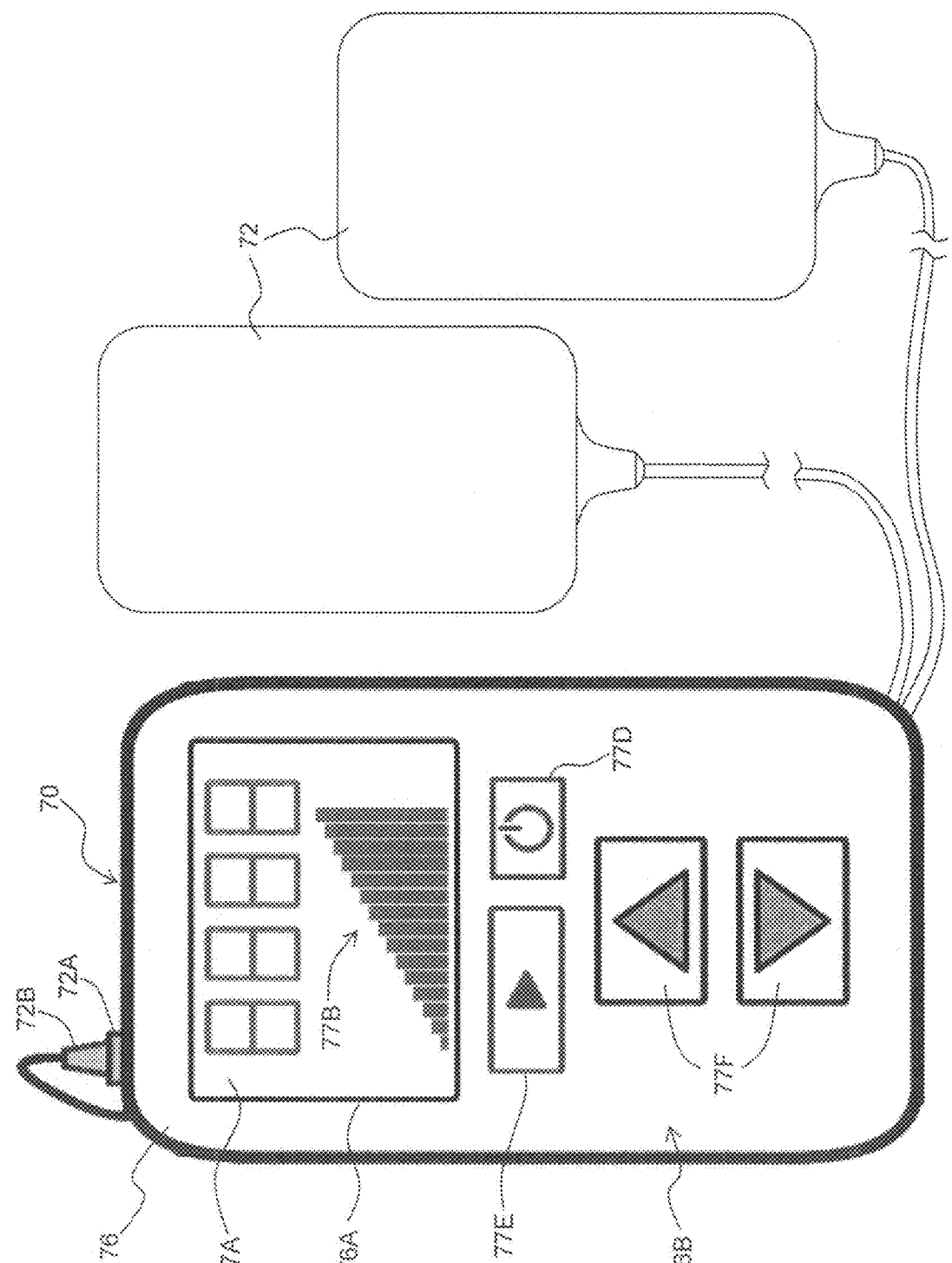
FIG. 14 is a front view showing an external appearance of the frequency therapy device.

As shown in FIG. 13 (a block diagram) and FIG. 14 (a front view showing an external appearance), a frequency therapy device 70 according to the second embodiment of the present invention is configured to include: a pair of electrode pads 72 capable of being in contact with the human body with an affected part being interposed therebetween; a main device unit 80 that passes, between the pair of electrode pads 72, a current corresponding to a voltage waveform in which the direction thereof is reversed at regularly repeated time intervals and a voltage increases and decreases alternately on a positive side and a negative side; a display unit 76A connected to the main device unit 80 for displaying a magnitude of a voltage applied between the electrode pads 72 and a code; an operation/display panel 76 including a panel operation switch unit 76B for operating the main device unit 80; and a battery 90 incorporated in the main device unit 80.

The main device unit 80 includes: a waveform memory 82 that stores a plurality of voltage waveforms at different frequencies; and a central control unit (hereinafter, referred to as a CPU) 100 that is configured to sequentially read the plurality of voltage waveforms stored in the waveform memory 82 and pass a current corresponding to the read voltage waveform between the pair of electrode pads 72.

The waveform memory 82 is what is called a sound source memory, and stores a voltage waveform, for each of a plurality of frequencies, as waveform data formed with a sampling frequency of 192 kHz or higher and a number of quantization bits of 24 bits or more as mentioned above.

The CPU 100 is configured to read waveform data from the waveform memory 82 for each frequency, output the waveform data to a D/A converter 84 so as to be converted to an analog waveform during a preset time for the frequency, and pass a current corresponding to the voltage waveform between the electrode pads 72.

In addition to the waveform memory 82 and the D/A converter 84 described above, the main device unit 80 includes: an output drive 86; an alarm 96; and a minus voltage control unit 98.

The D/A converter 84 is configured to perform a digital-analog conversion on the waveform data read from the waveform memory 82 by the CPU 100 with a sampling frequency of 192 kHz or higher and a number of quantization bits of 24 bits or more and output the waveform data to the output drive 86 in an analog waveform.

The output drive 86 is configured to change an output from the battery 90 on the basis of the aforementioned analog waveform and provide the changed output to the respective electrode pads 72.

The CPU 100 controls the output drive 86 to provide an output in accordance with a command signal from the panel operation switch unit 76B.

A program memory 94 stores therein a program for operating the CPU 100. The alarm 96 is configured to emit an alarm when a condition to be notified to a patient occurs, including the end of therapy.

As mentioned above, the minus voltage control unit 98 displaces the 0-V level in a voltage waveform toward the plus side by 5% to 10% of the maximum voltage from the intermediate position in the waveform chart, so that an amount of electrons entering the human body through the electrode pads 72 becomes greater than an amount of electrons escaping from the body. In this manner, the minus voltage control unit 98 prevents the effects of deficiency in electrons on the human body. Here, the reason for being set to 5% or more is because deficiency in electrons in the human body can be prevented from occurring even when a source voltage fluctuates. The reason for being set to 10% or less is to prevent surplus in electrons.

As shown in FIG. 14, the display unit 76A of the operation/display panel 76 is configured to include: a numerical value display section 77A that displays a code number or a code value, and a remaining time of therapy; and a graph display section 77B that displays an output.

A power switch 77D, a START/PAUSE switch 77E for starting/pausing/resuming therapy, and an up-down setting switch 77F for increasing or decreasing output intensity from the output drive 86 and setting a code number or a code value are disposed in the panel operation switch unit 76B.

The reference numeral 72A in FIG. 14 denotes a jack for receiving a plug 72B of the electrode pads 72.

A configuration of the CPU 100 and the waveform memory 82 will be described next.

Figure 15:
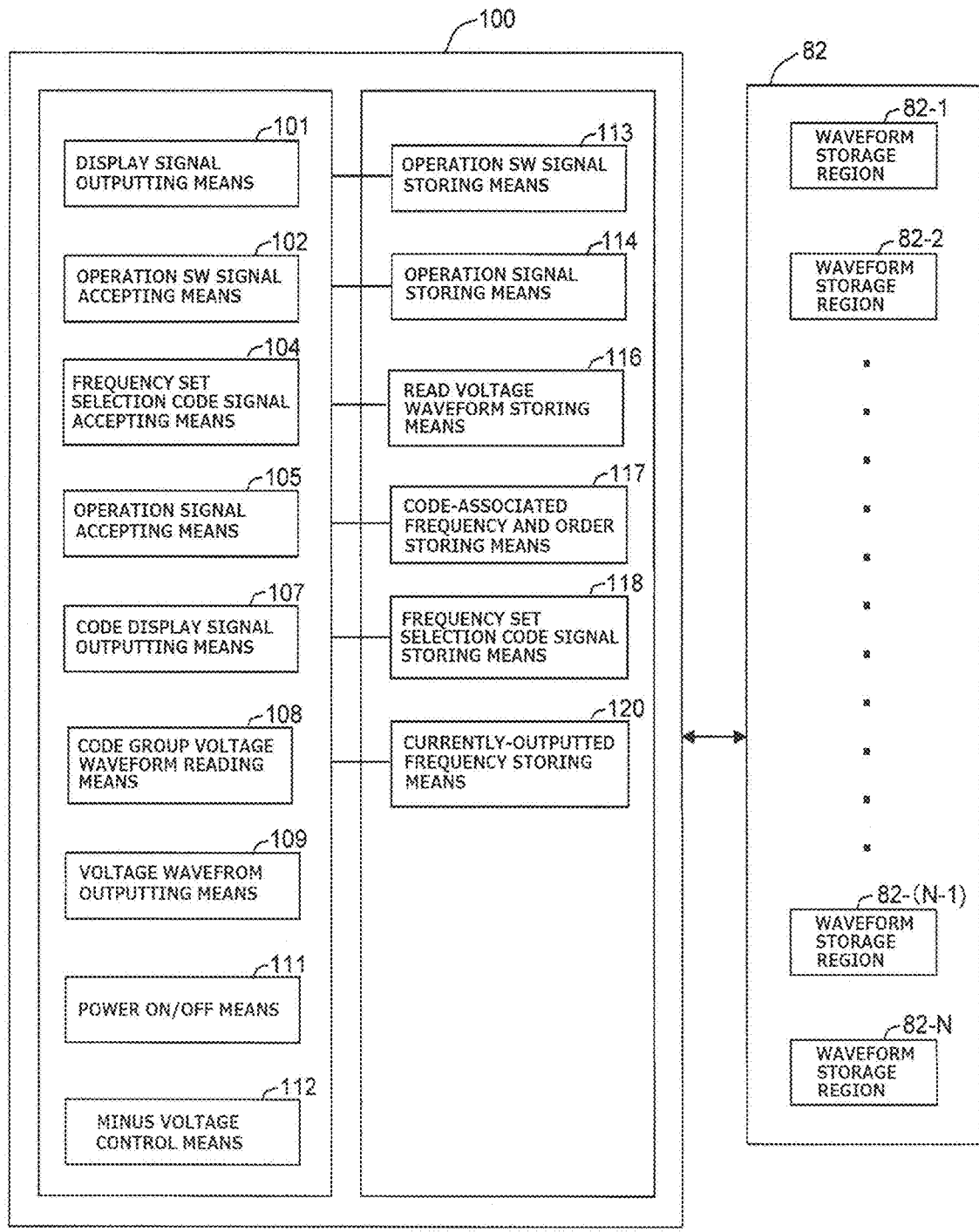
FIG. 15 is a block diagram showing general configurations of a central control unit and a waveform memory in the frequency therapy device.

As shown in FIG. 15, the CPU 100 is configured to include: a display signal outputting means 101; an operation switch signal accepting means 102; a frequency set selection code signal accepting means 104; an operation signal accepting means 105; a code display signal outputting means 107; a code group voltage waveform reading means 108; a voltage waveform outputting means 109; a power ON/OFF means 111; a minus voltage control means 112; an operation switch signal storing means 113; an operation signal storing means 114; a read voltage waveform storing means 116; a code-associated frequency and order storing means 117; a frequency set selection code signal storing means 118; and a currently-outputted frequency storing means 120.

The display signal outputting means 101 is configured to display, at the numerical value display section 77A and the graph display section 77B in the display unit 76A, output intensity, and a code number or a code value operated by the up-down setting switch 77F in the operation/display panel 76.

The operation switch signal accepting means 102 is configured to accept operation signals from the panel operation switch unit 76B of the operation/display panel 76. Moreover, the accepted signals are stored in the operation switch signal storing means 113.

The operation signal accepting means 105 is configured to accept operation signals transmitted from the panel operation switch unit 76B. The accepted operation signals, specifically, an output intensity signal and the aforementioned code number signal, are stored in the operation signal storing means 114.

The code display signal outputting means 107 is configured to display an inputted code number at the display unit 76A on the basis of a display signal stored in the operation switch signal storing means 113.

The code-associated frequency and order storing means 117 stores, corresponding to a code, a plurality of frequencies predefined, for each code, to be included in the code and their output order. As shown in the aforementioned Table 1, for example, a frequency set selection code and the first to the n-th frequencies (n is a natural number greater than or equal to two) are stored in combination. Specifically, for the code number 1231, 20 Hz, 880 Hz, 5 kHz, . . . , 10 kHz are stored in this order.

On the basis of an inputted code signal and information stored in the code-associated frequency and order storing means 117, the code group voltage waveform reading means 108 is configured to sequentially read, from the waveform memory 82, the voltage waveforms at the plurality of frequencies included in the code.

The voltage waveform outputting means 109 is configured to output, to the D/A converter 84, data on the voltage waveforms at the frequencies read by the code group voltage waveform reading means 108.

The power ON/OFF means 111 is configured to turn on or off the output of the battery 90 to the output drive 86 in accordance with an operation of the power switch 77D.

The currently-outputted frequency storing means 120 is configured to store the frequency of the waveform data being currently outputted from the voltage waveform outputting means 109.

The operation switch signal accepting means 102 is configured to turn off the output of the battery 90 to the output drive 86 so as to interrupt current supply from the output drive 86 when an interruption signal for interrupting therapy is inputted during therapy provided by the frequency therapy device 70.

The code group voltage waveform reading means 108 in this case is configured to read frequency information at the time of the interruption, which has been stored in the currently-outputted frequency storing means 120, and read the voltage waveform at that frequency when the therapy is resumed.

The waveform memory 82 includes N (N is a natural number greater than or equal to two) waveform storage regions 82-1 to 82-N, and the number of therapy frequencies used in the frequency therapy device 70 in this embodiment is N. Voltage waveforms at the N frequencies are stored in any of the waveform storage regions 82-1 to 82-N for each frequency.

The other elements are the same as those of the first embodiment, and thus the detailed description thereof will be omitted.

Figure 16:
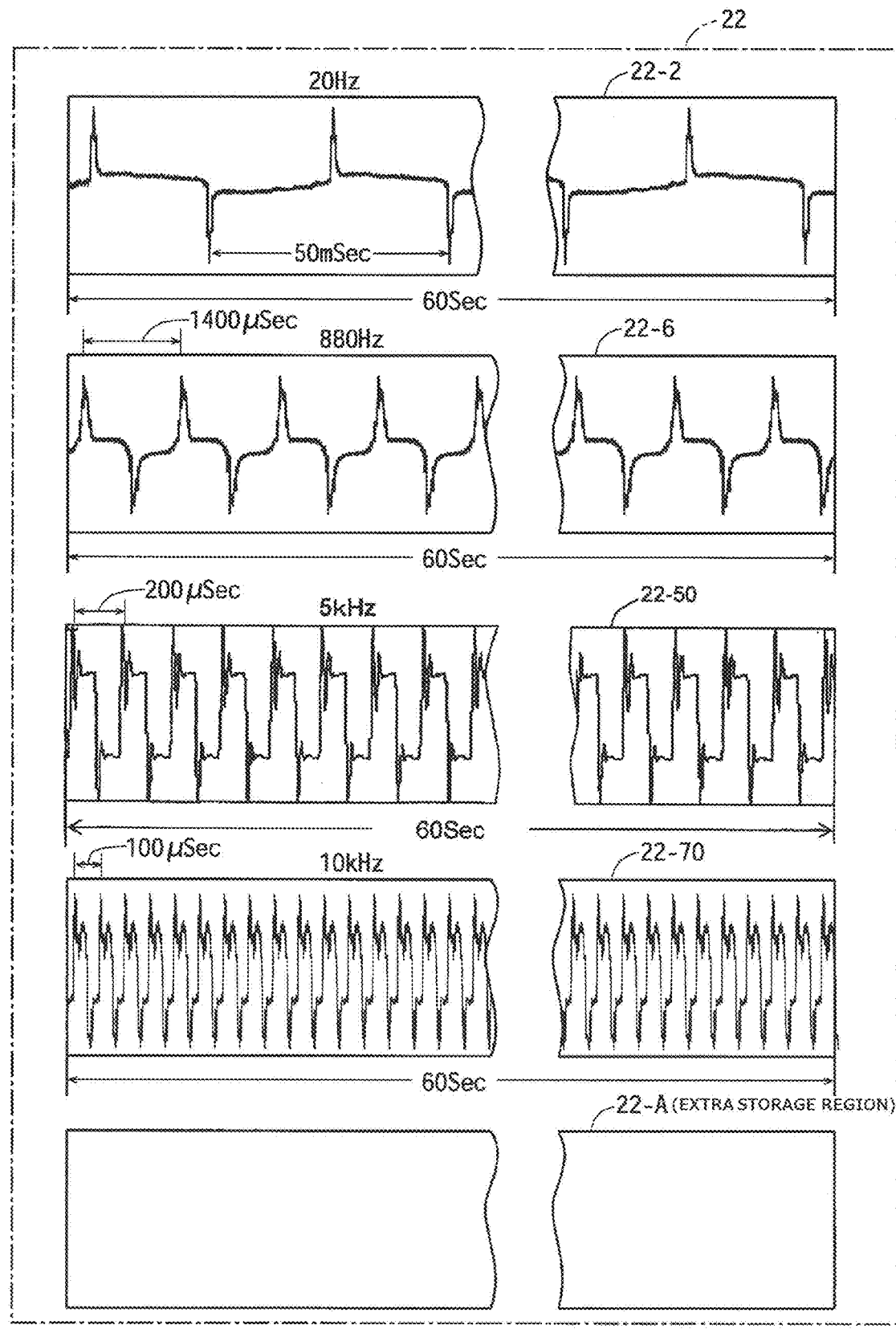
FIG. 16 is a chart similar to FIG. 5, showing a state in which voltage waveforms are stored in the waveform memory in a divided manner for one minute each.

While a voltage waveform is successively stored for three minutes in each of the waveform storage regions 22-1 to 22-N in the waveform memory 22 in the above-described first embodiment, the present invention is not limited thereto. When the voltage waveform storage capacity of the waveform memory 22 is insufficient, for example, voltage waveforms maybe stored only for a time obtained by dividing a set time (three minutes in the embodiment) by two or three, and the voltage waveforms maybe read twice or three times for a single duration of the set time. FIG. 16 shows a case where three minutes are divided into three, and voltage waveforms are read three times for one minute each.

In the above-described embodiments, the sampling frequency is 192 kHz and the number of quantization bits is 24 bits. This is because what is called a sound source chip is used as the waveform memory and the upper limit of the sound chip corresponds to 192 kHz and 24 bits. The present invention can be also applied to cases exceeding 192 kHz and 24 bits.

Figure 17:
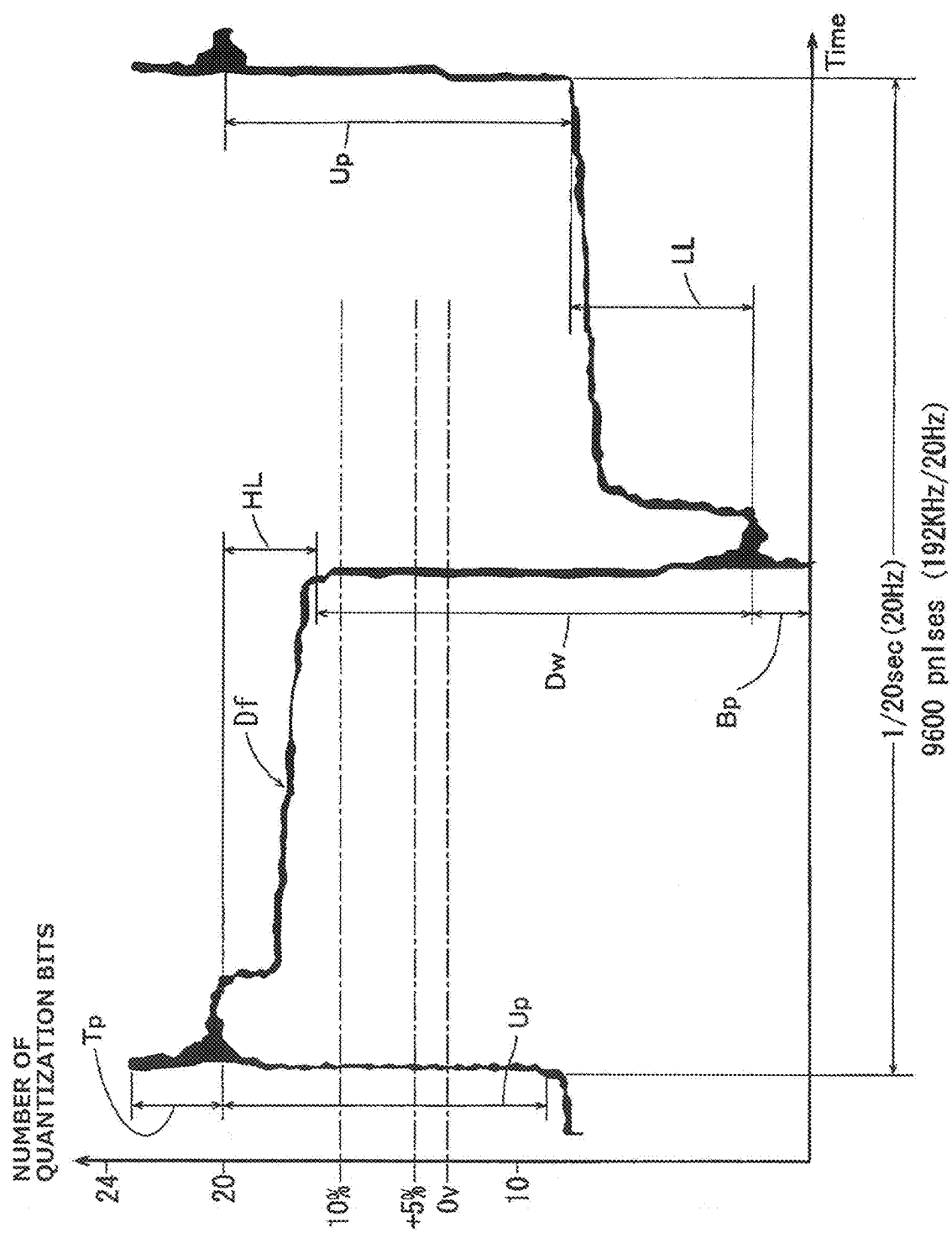
FIG. 17 is a chart showing a voltage waveform stored in a waveform memory of a frequency therapy device according to a third embodiment of the present invention.

As shown in FIG. 6, in the voltage waveform (waveform data) stored in the waveform memory in the above-described first embodiment, a voltage in the high-level part HL has a maximum value of +5 V and a voltage in the low-level part LL has a minimum value of −5 V. These values are set to be significantly smaller than those of the sharp-pointed top peak part Tp and the sharp-pointed bottom peak part Bp. For a patient less likely to feel pain for current, voltages (absolute values) in the high-level part HL and the low-level part LL can be set larger than the above-described values as in a voltage waveform of a third embodiment shown in FIG. 17, for example.

In this case, a deformed state of diseased cells that is caused by an impact given to the human body by the sharp-pointed top peak part Tp and the sharp-pointed bottom peak part Bp can be more reliably kept until the start of deformation due to an impact in the reverse direction.

INDUSTRIAL APPLICABILITY

The present invention can be applied to the field of frequency therapy devices such as low-frequency therapy devices.

REFERENCE SIGNS LIST 10, 70 . . . frequency therapy device
12, 14, 72 . . . electrode pad
12A . . . jack (first output channel)
14A . . . jack (second output channel)
16, 76 . . . operation/display panel
16A, 77D . . . power switch
16B . . . group of setting switches
16B1 . . . SET switch
16B2 . . . output channel (CH) selection switch
16B3 . . . code setting dial
16B4 . . . RECORD switch
16B5 . . . CLEAR switch
16C . . . code information display unit
16C1 . . . number up-down switch
16C2 . . . code number display unit
16C3 . . . output CH display unit
16C4 . . . code value display unit
16C5 . . . code time display unit
16D . . . remaining therapy time display unit
16E . . . current display unit
16F, 77E . . . START/PAUSE switch
16G . . . output increase or decrease switch
16H . . . output display unit
16I . . . LED for indicating that output power is on
17 . . . IR remote control reception unit
18 . . . IR remote control transmitter
18F . . . remote control START/PAUSE switch
18G . . . remote control output increase or decrease switch
20, 80 . . . main device unit
22, 82 . . . waveform memory
21-1 to 22-N, 82-1 to 82-N . . . waveform storage region
22-A . . . extra storage region
24, 84 . . . D/A converter
26 . . . output drive set
26A, 26B, 86 . . . output drive
28 . . . switching power adapter
30 . . . DC/DC converter
32 . . . regulator
34, 94 . . . program memory
36 . . . notification sound output system
36A, 84 . . . D/A converter
36B . . . amplifier
36C . . . loudspeaker
38, 98 . . . minus voltage control unit
40, 100 . . . central control unit (CPU)
41, 101 . . . display signal outputting means
42, 102 . . . operation switch signal accepting means
43 . . . output channel selection signal accepting means
44, 104 . . . frequency set selection code signal accepting means
45, 105 . . . operation signal accepting means
46 . . . frequency set selection code output order and output mode selection setting accepting means
47, 107 . . . code display signal outputting means
48, 108 . . . code group voltage waveform reading means
49, 109 . . . voltage waveform outputting means
50 . . . DC/DC converter driving means
51, 111 . . . power ON/OFF means
52, 112 . . . minus voltage control means
53, 113 . . . operation switch signal storing means
54, 114 . . . operation signal storing means
55 . . . output channel selection signal storing means
56, 116 . . . read voltage waveform storing means
57, 117 . . . code-associated frequency and order storing means
58, 118 . . . frequency set selection code signal storing means
59 . . . frequency set selection code output order and output mode selection setting storing means
60, 120 . . . currently-outputted frequency storing means
76A . . . display unit
76B . . . panel operation switch unit
77A . . . numerical value display section
77B . . . graph display section
77F . . . up-down setting switch
90 . . . battery
96 . . . alarm
98 . . . minus voltage control unit

The invention claimed is:

1. A frequency therapy device comprising: at least a pair of electrode pads capable of being in contact with a human body with an affected part being interposed therebetween; a main device unit that passes, between the pair of electrode pads, a current corresponding to a voltage waveform in which a direction thereof is reversed at regularly repeated time intervals and a voltage increases and decreases alternately on a positive side and a negative side; a display unit connected to the main device unit for displaying a magnitude of a voltage applied between the pair of electrode pads; and an operation/display panel for operating the main device unit, wherein
   the main device unit includes: a waveform memory that stores a plurality of voltage waveforms at different frequencies; and
   a central control unit configured to selectively read the plurality of voltage waveforms stored in the waveform memory, and repeatedly and successively use the read voltage waveform to pass a current between the pair of electrode pads,
   the waveform memory stores the voltage waveform, for each of the plurality of frequencies, as waveform data comprising a square wave with a sampling frequency of 192 kHz or higher and a number of quantization bits of 24 bits or more, and
   the central control unit is configured to read the waveform data from the waveform memory for each frequency, convert the waveform data to an analog waveform by a D/A converter during a preset time for the frequency, and pass a current corresponding to the voltage waveform between the pair of electrode pads, the waveform data stored in the waveform memory has, within a single waveform period, a waveform ranging from a rise part heading toward a positive region during a rise transition period, through a sharp-pointed top peak part having an overshoot shape at an end of the rise, a high-level part having a smaller value than that of the sharp-pointed top peak part, a fall part heading toward a negative region during a fall transition period, a sharp-pointed bottom peak part having an undershoot shape at an end of the fall, and a low-level part having a larger value than that of the sharp-pointed bottom peak part, to a next rise part, and in a frequency range of at least 1000 Hz or lower, the waveform data stored in the waveform memory has, within a single waveform period, a waveform ranging from a rise part heading toward a positive region from a 0-V level during a rise transition period, through a sharp-pointed top peak part, Tp, having a spike shape at an end of the rise and having a pulse width $W_{tp}$ of 30 μsec to 200 μsec, a high-level part in which the voltage is larger than 0 V and smaller than or equal to 5 V, a fall part heading toward a negative region during a fall transition period, a sharp-pointed bottom peak part, Bp, having a spike shape at an end of the fall and having a pulse width $W_{bp}$ of 30 μsec to 200 μsec, and a low-level part in which the voltage is smaller than 0 V and larger than or equal to −5 V, to a next rise part.

2. The frequency therapy device according to claim 1, wherein a peak-part-immediately-following fall part that is located immediately after the sharp-pointed top peak part and immediately before the high-level part, and a peak-part-immediately-following rise part that is located immediately after the sharp-pointed bottom peak part and immediately before the low-level part are included.

3. The frequency therapy device according to claim 1, wherein a voltage in the peak-part-immediately-following fall part is set to 50% to 65% of a voltage in the sharp-pointed top peak part, and a voltage in the peak-part-immediately-following rise part is set to 50% to 65% of a voltage in the sharp-pointed bottom peak part.

4. The frequency therapy device according to claim 1, wherein the waveform memory includes a plurality of storage regions for storing the waveform data, one storage region of the plurality of storage regions repeatedly and successively stores, for each frequency, waveform data during a set time, and the central control unit is configured to read, at one time, the waveform data for the set time that is stored in the one storage region of the waveform memory, convert the read waveform data to an analog waveform, and pass the analog waveform between the pair of electrode pads.

5. The frequency therapy device according to claim 4, wherein the set time equals three minutes.

6. The frequency therapy device according to claim 1, wherein the waveform memory includes a plurality of storage regions for storing the waveform data, one storage region of the plurality of storage regions repeatedly and successively stores, for each frequency, waveform data during a set time, and the central control unit is configured to read, at two to five times, the waveform data for the set time that is stored in the one storage region of the waveform memory, convert the read waveform data to an analog waveform, and sequentially pass the analog waveform between the pair of electrode pads.

7. The frequency therapy device according to claim 1, wherein the central control unit stores two or more different frequency set selection codes, pieces of waveform data for a plurality of frequencies preset, for each of the frequency set selection codes, so as to correspond to the frequency set selection code, and an order when the pieces of waveform data are read, and the central control unit is configured to sequentially read, and then output, when the frequency set selection code is inputted, the pieces of waveform data for the plurality of frequencies preset corresponding to the frequency set selection code in the predefined order during a set time.

8. The frequency therapy device according to claim 7, wherein
the central control unit includes: a code-associated frequency and order storing means that stores the frequency set selection code, frequencies corresponding to the frequency set selection code, and an output order of pieces of waveform data for the frequencies;
a frequency set selection code signal accepting means that selects the frequency set selection code, and a code group voltage waveform reading means that reads, from the waveform memory, the pieces of waveform data for the frequencies for each of the frequency set selection codes in the order stored in the code-associated frequency and order storing means on a basis of the accepted frequency set selection code signal; and
a voltage waveform outputting means that outputs the pieces of waveform data read by the code group voltage waveform reading means in the order.

9. The frequency therapy device according to claim 8, wherein
the frequency set selection code signal accepting means is configured to sequentially accept a plurality of the frequency set selection codes, and the code group voltage waveform reading means is configured to read, in an order of the frequency set selection codes accepted by the frequency set selection code signal accepting means, pieces of waveform data for each of the frequency set selection codes.

10. The frequency therapy device according to claim 8, wherein the main device unit includes:
two output drives that form a voltage waveform to be applied between the at least a pair of electrode pads by applying a voltage to the analog waveform from the D/A converter;
a direct-current power unit that supplies a direct current to the output drives; and
two pairs of electrode pads independently connected to the two output drives, and
the central control unit is configured to select a one-of-the-pair output mode in which a direct current is supplied only to one of the two output drives and no direct current is supplied to the other one of the two output drives, or a both output mode in which a direct current is simultaneously supplied to the two output drives so as to form the same voltage waveform.

11. The frequency therapy device according to claim 10, wherein
the central control unit includes: a frequency set selection code output order and output mode selection setting accepting means that accepts a selection setting for an order of up to 11 frequency set selection codes and a selection setting as to whether the one-of-the-pair output mode or the both output mode for each of the frequency set selection codes; and
a frequency set selection code output order and output mode selection setting storing means that stores the accepted frequency set selection code, output order, and output mode selection setting signal.

12. The frequency therapy device according to claim 1, wherein when each of the pulse widths $W_{tp}$ and $W_{bp}$ of the sharp-pointed top peak part Tp and the sharp-pointed bottom peak part Bp is set to 60 μsec or less.

* * * * *